United States Patent [19]

Abood et al.

[11] Patent Number: 5,424,334
[45] Date of Patent: Jun. 13, 1995

[54] PEPTIDE MIMETIC COMPOUNDS USEFUL AS PLATELET AGGREGATION INHIBITORS

[75] Inventors: Norman A. Abood, Morton Grove; Robert B. Garland; Masateru Miyano, both of Northbrook, all of Ill.

[73] Assignee: G. D. Searle & Co., Chicago, Ill.

[21] Appl. No.: 810,791

[22] Filed: Dec. 19, 1991

[51] Int. Cl.$^6$ .................. C07C 257/18; A61K 31/325
[52] U.S. Cl. .................................. 514/562; 514/428; 514/471; 514/533; 514/563; 548/565; 544/321; 560/29; 562/430; 562/440
[58] Field of Search .................. 566/29; 562/430, 440; 549/321; 548/565; 514/428, 471, 533, 563, 562

[56] References Cited

U.S. PATENT DOCUMENTS

| | | | |
|---|---|---|---|
| 4,073,891 | 2/1978 | Okamoto et al. | |
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,791,102 | 12/1988 | Bernat et al. | 514/19 |
| 4,857,508 | 8/1989 | Adams et al. | 514/18 |
| 4,879,313 | 11/1989 | Tjoeng et al. | 514/616 |
| 4,977,168 | 12/1990 | Bernat et al. | |

FOREIGN PATENT DOCUMENTS

| | | | |
|---|---|---|---|
| 2593812 | 8/1987 | European Pat. Off. | C07K 5/02 |
| 0275748 | 7/1988 | European Pat. Off. | |
| 0298820 | 1/1989 | European Pat. Off. | |
| 0352249 | 1/1990 | European Pat. Off. | C07K 5/06 |
| 0372486 | 6/1990 | European Pat. Off. | |
| 0381033 | 8/1990 | European Pat. Off. | |
| 0410540 | 1/1991 | European Pat. Off. | |
| 0445796 | 9/1991 | European Pat. Off. | C07K 5/06 |
| 0502536 | 9/1992 | European Pat. Off. | C07K 5/02 |
| 2007663 | 5/1979 | United Kingdom | C07C 143/80 |

OTHER PUBLICATIONS

D. Haverstick et al. Inhibition of Platelet Adhesion to etc. Blood 66(4) 946–952 Oct. 1985.
E. Ruoslahti et al. New Perspectives in Cell Adhesion: RGD and etc. Science 23 491–497 Oct. 1987.
R. Gould et al. Disintegrins: A Family of Integrin Inhibitory etc. Proc. Soc. Exp. Biol. and Med. 195(2) 168–171 Nov. 1990.
M. Goodman et al. On The Concept of Linear Modified etc. Accounts of Chemical Research 12(1) 1–7 Jan. 1979.
M. Kloczewiak et al. Platelet Receptor Recognition Site on Human etc. Biochemistry 23(8) 1767–1774 Jan. 1984.
Z. Ruggeri et al. Inhibition of Platelet Function with Synthetic etc. Proc. Natl. Acad. Sci., USA 83 5708–5712 Aug. 1986.
E. Plow et al. The Effect of Arg–Gly–Asp-Containing Peptides etc. Proc. Natl. Acad. Sci., USA 82 8057–8061 Dec. 1985.
M. Ginsberg et al. Inhibition of Fibronectin Binding to Platelets etc. The Journal of Biological Chemistry 260(7) 3931–3936 Apr. 1985.

*Primary Examiner*—Robert Gerstl
*Attorney, Agent, or Firm*—Joy Ann Serauskas; Roger A. Williams

[57] ABSTRACT

This invention relates to compounds having the following formula

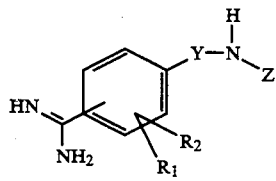

or a pharmaceutically acceptable salt which are useful in the inhibition of platelet aggregation. This invention also relates to pharmaceutical compositions—of such phenyl amidines derivatives.

26 Claims, No Drawings

PEPTIDE MIMETIC COMPOUNDS USEFUL AS PLATELET AGGREGATION INHIBITORS

FIELD OF THE INVENTION

This invention is in the field of mammalian therapeutics and relates to compounds for the treatment of mammalian disorders such as cardiovascular disorders. Of particular interest is a class of phenyl amidine derivatives useful as inhibitors of platelet aggregation.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Hayerstick et al., *Blood* 66 (4), 946–952 (1985); and Ruoslahti and Pierschbacher, *Science* 238, 497–497 (1987). Still other such inhibitory peptides are disclosed in EP Patent Applications 275,748 and 298,820.

U.S. Pat. No. 4,879,313 discloses compounds useful as inhibitors of platelet aggregation having the formula:

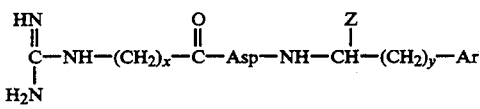

wherein
x = 6 to 10,
y = 0 to 4,
Z = H, COOH, CONH$_2$ OR C$_{1-6}$ alkyl,

Ar = phenyl, biphenyl or naphthyl, each substituted with 1 to 3 methoxy groups, or an unsubstituted phenyl, biphenyl, naphthyl, pyridyl or thienyl group, and Asp = aspartic acid residue.

This art is structurally distinct from the present invention because it lacks the phenylamidine moiety.

U.S. Pat. No. 4,977,168 discloses compounds having the following structural formula:

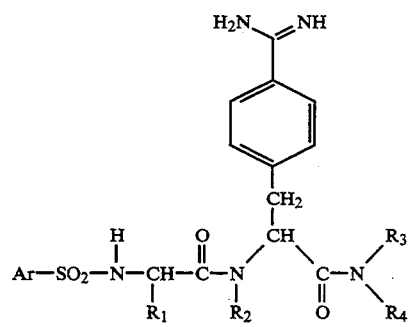

wherein
R$_1$ represents hydrogen, a lower alkyl group, a lower hydroxyalkyl group, a benzyl group, a phenyl group or a 4-hydroxyphenyl group;

R$_2$ represents a lower alkyl, lower alkenyl, lower alkynyl or benzyl group, or a lower alkoxycarbonylalkyl, lower carboxyalkyl, or lower hydroxyalkyl group;

R$_3$ and R$_4$, identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted or substituted by an alkoxycarbonyl or carboxy group, piperazino, 4-(lower alkyl)piperazino, 4-(lower hydroxyalkyl)piperazino, or piperidino not substituted or substituted by one of the following groups: lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group, possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids which are useful as antithrombotic agents. These compounds are structurally distinct from the present invention because they are arylsulphonylaminoacyl aminophenylalaninamide derivatives in contrast to the compounds of the present invention which are propanoic acid esters-1-amidinophenyl alkylamino carbonyl derivatives.

U.S. Pat. No. 4,791,102 discloses compounds having the following structural formula

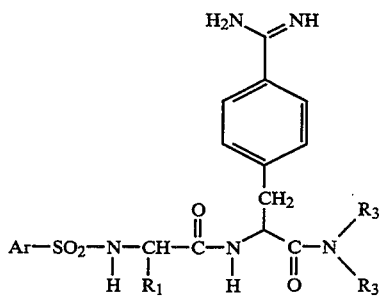

wherein

R₁ represents a lower alkyl, lower hydroxyalkyl, or benzyl group, a phenyl or a 4-hydroxyphenyl group.

R₂ and R₃, identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group. Ar represents a phenyl, a possibly substituted alpha-naphthyl or beta-naphthyl group, or else a heteroaryl group chosen from pyridyl, quinolinyl, isoquinolinyl, possibly substituted which are useful as selective inhibiting agents of thrombin and antithrombotics. These compounds are structurally distinct from the present invention because they are arylsulphonylaminoacyl aminophenylalaninamide derivatives in contrast to the compounds of the present invention which are propanoic acid esters-1-amidinophenyl alkylamino carbonyl derivatives.

European Patent Application 372,486 discloses N-acyl beta amino acid derivatives of the formula:

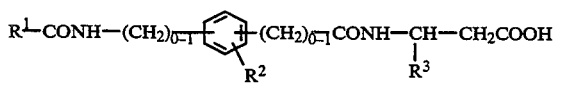

and their salts. Said compounds are useful for inhibiting platelet aggregation in the treatment of thrombosis, stroke, myocardial infarction, inflammation and arteriosclerosis, and for inhibiting metastasis.

European Patent Application 381,033 A1 discloses amidino or guanidino-aryl substituted alkanoic acid derivatives which are useful for the treatment of thrombosis, apoplexy, cardiac infarction, inflammation, arteriosclerosis and tumors. These compounds are structurally distinct from the present invention because they are aryl acetic acid/esters 2-amidino/guanidino substituted phenyl alkyl carbonyl amino derivatives in contrast to the compounds of the present invention which are propanoic acid/esters-1-amidinophenylalkyl aminocarbonyl derivatives.

European Patent Application 445,796 A2 discloses acetic acid derivatives having the formula

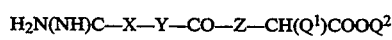

where

Q¹ stands for hydrogen, methyl or phenyl,

Q² stands for hydrogen, phenyl-low-alkyl or low alkyl that can be cleaved under physiological conditions, X stands for 1,4-phenylene, 2,5- or 3,6-pyridylene or, 1,4-piperidinylene, which is bonded to group Y through the C atom in the 4-position, Y is a group having the formula

| | |
|---|---|
| —(CH₂)₀₋₂—CONHCH(Q³)(CH₂)₁₋₃ | (Y¹) |
| —CONHCH₃CH(Q⁴) | (Y²) |
| —(CH₂)₃NHCOCH₂— | (Y³) |
| —NHCO(CH₂)₃— | (Y⁴) |

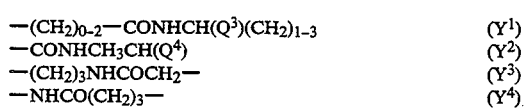

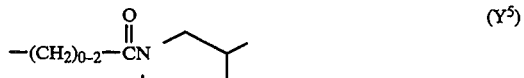

OR

where

Q³ stands for hydrogen, methyl, phenyl, —COOH, —COO—low-alkyl, —CONH(CH₂)₂—COOH or —CONH(CH₂)₂—COO-low-alkyl, Q⁴ hydrogen, methyl or phenyl, Z a 1,4-piperazinylene group, a 1,4-piperazinylene group which is bonded to the CO group through the N atom in the 1-position or a group having the formula —NHCH(R¹)— or —NHCH(COR²)— where

R¹ stands for hydrogen, methyl, phenyl or a —COO-low-alkyl,

R² stands for the residue of an α-aminocarboxylic acid bonded through the amino group or of an ester or amide thereof, or a group having the formula —NHCH₂CH₂—Ar, or —CO—R², or, if applicable, a mono- or di-low-alkylated carbamoyl group or a pyrrolidinoyl or piperidinoyl group, Ar stands for a phenyl or a phenyl substituted by low alkyl, low alkoxy, —COOH, —COO-low-alkyl, —O(CH₂)₁₋₄—COOH, —O(CH₂)₁₋₄—COO-low-alkyl, —CONH₂, —CONH-low-alkyl, —CON(-low alkyl)₂, pyrrolidinoyl or piperidinoyl which are said to have inhibitory action on the bonding of adhesive proteins to blood platelets as well as blood platelet aggregation and cell-cell adhesion. These compounds are structurally distinct from the present invention because they contain a second, mandatory carbonyl group.

Goodman, et al., *Accounts of Chemical Research* 12, No. 1, 1–7 (January 1979) discloses a stereochemical analysis of retro-isomers of cyclic and linear peptides.

SUMMARY OF THE INVENTION

The present invention relates to a class of compounds represented by the formula

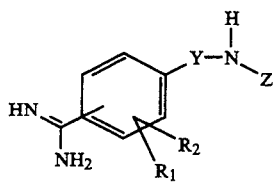

I or a pharmaceutically acceptable salt thereof, wherein
R₁ and R₂ are each independently hydrido, alkyl having 1 to 6 carbon atoms, alkoxy having 1 to 6 carbon atoms or halo;
Y is alkylene having 1 to 6 carbon atoms, alkenylene having 2 to 4 carbon atoms, alkynylene having 2 to 4 carbon atoms or carboxamidoalkyl wherein the alkyl is 1 to 6 carbon atoms and
Z is a group having the formula

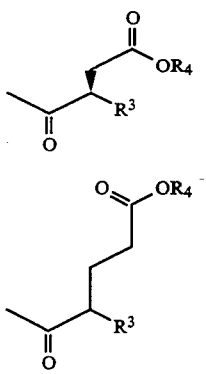

wherein
R₃ is alkyl having 1 to 6 carbon atoms; alkenyl having 2 to 4 carbon atoms; alkynyl having 2 to 4 carbon atoms; phenyl; substituted phenyl wherein each substituent can be selected from the group consisting of alkyl having 1 to 6 carbon atoms and alkoxy having 1 to 6 carbon atoms; phenylalkylamido wherein the alkyl is 1 to 6 carbon atoms and the alkyl chain may be interrupted by oxygen; substituted phenylalkylamido wherein the alkyl is 1 to 6 carbon atoms and the alkyl chain may be interrupted by oxygen and the phenyl substituents are selected from the group consisting of alkyl having 1 to 6 carbon atoms and alkoxy having 1 to 6 carbon atoms; hydroxy; amino; 5 or 6 carbon membered cyclic ring wherein one or two of the ring carbon atoms are replaced by a hetero atom which is selected from nitrogen, oxygen and sulfur with the proviso that when two hetero atoms are present one hetero atom must be nitrogen; alkylsulfonamido wherein the alkyl is 1 to 6 carbon atoms; phenylsulfonamido; or substituted phenylsulfonamido wherein each phenyl substituent can be selected from the group consisting of alkyl having 1 to 6 carbon atoms, alkoxy having 1 to 6 carbon atoms, and halo; and
R₄ is absent, hydrido or alkyl having 1 to 6 carbon atoms with the understanding that when R₄ is absent, and R₃ is absent or alkyl having 1 or 2 carbon atoms, the oxygen adjacent to R₄ position can combine with R₃ when present or can combine with the carbon adjacent to the carbonyl to form a lactone; with the proviso that when Y is alkyl having three carbon atoms Z is Z₁.

The invention further relates to pharmaceutical compositions comprising a compound of formula I. Such compounds and compositions have usefulness as inhibitors of platelet aggregation. The invention also relates to a method of inhibiting platelet aggregation in a mammal in need of such treatment.

A preferred embodiment of the present invention is a compound of the formula

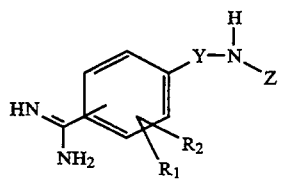

I or a pharmaceutically acceptable salt thereof, wherein
R₁ and R₂ are each independently hydrido, alkyl having 1 to 6 carbon atoms, alkoxy having 1 to 6 carbon atoms or halo.
Y is alkylene having 1 to 6 carbon atoms, alkenylene having 2 to 4 carbon atoms or alkynyl having 2 to 4 carbon atoms;
Z is a group having the formula

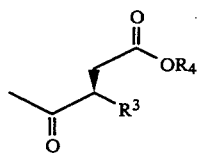

or

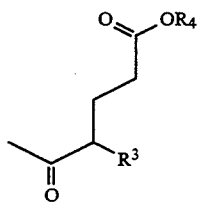

wherein
R₃ is phenylalkylamido wherein the alkyl is 1 to 6 carbon atoms and the alkyl chain may be interrupted by oxygen; substituted phenylalkylamido wherein the alkyl is 1 to 6 carbon atoms and the alkyl chain may be interrupted by oxygen and the phenyl substituents are selected from the group consisting of alkyl having 1 to 6 carbon atoms and alkoxy having 1 to 6 carbon atoms; and
R₄ is hydrido or alkyl having 1 to 6 carbon atoms.
Exemplifying this embodiment are the following compounds:
4-[[4-[4-(aminoiminomethyl)phenyl]butyl]amino]-4-oxo-3R-[[(phenylmethoxy)carbonyl]amino]butanoic acid;
5-[[4-[4-(aminoiminomethyl)phenyl]butyl]amino]-5-oxo-4R-[[(phenylmethoxy)carbonyl]amino]pentanoic acid;

5-[[4-[4-(aminoiminomethyl)phenyl]butyl]amino]-5-oxo-4S-[[(phenylmethoxy)carbonyl]amino]pentanoic acid;

5-[[4-[4-(aminoiminomethyl)phenyl]butyl]amino]-5-oxo-4S-[1-oxo-3-phenylpropylamino]pentanoic acid;

4-[[4-[4-(aminoiminomethyl)phenyl]butyl]amino]-4-oxo-3R-[(1-oxo-3-phenylpropyl)amino]butanoic acid;

ethyl 5-[[4-[4-(aminoiminomethyl)phenyl]butyl]amino]-5-oxo-4R-[[(phenylmethoxy)carbonyl]amino]pentanoate, monohydrochloride; and 5-[[5-[4-(aminoiminomethyl)phenyl]-4-pentynyl]amino]-5-oxo-4R-[[(phenylmethoxy)carbonyl]amino]pentanoic acid A further preferred embodiment of the present invention is a compound of the formula

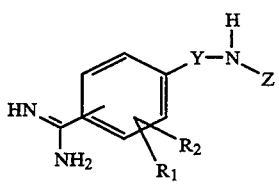

or a pharmaceutically acceptable salt thereof, wherein
R$_1$ and R$_2$ are each independently hydrido, alkyl having 1 to 6 carbon atoms, alkoxy having 1 to 6 carbon atoms or halo.

Y is alkylene having 1 to 6 carbon atoms, alkenylene having 2 to 4 carbon atoms or alkynylene having 2 to 4 carbon atoms;

Z is a group having the formula

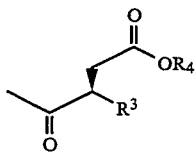 (Z$_1$)

or

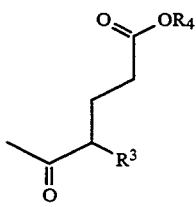 (Z$_2$)

wherein
R$_3$ is alkylsulfonamido wherein the alkyl is 1 to 6 carbon atoms; phenylsulfonamido, or substituted phenylsulfonamido wherein each phenyl substituent can be selected from the group consisting of alkyl having 1 to 6 carbon atoms, alkoxy having 1 to 6 carbon atoms; and R$_4$ is hydrido or alkyl having 1 to 6 carbon atoms.

Exemplifying this embodiment are the following compounds:

5-[[4-[4-(aminoiminomethyl)phenyl]butyl]amino]-5-oxo-4R-[(methylsulfonyl)amino]pentanoic acid;

ethyl 5-[[4-[4-(aminoiminomethyl)phenyl]butyl]amino]-5-oxo-4R-[(methylsulfonyl)amino]pentanoate, monohydrochloride; and 4-[[4-[4-(aminoiminomethyl)phenyl]butyl]amino]-4-oxo-3R-[[(4-methylphenyl)sulfonyl]amino]butanoic acid.

The invention further relates to pharmaceutical compositions comprising a compound of formula I. Such compounds and compositions have usefulness as inhibitors of platelet aggregation. The invention also relates to a method of inhibiting platelet aggregation in a mammal in need of such treatment.

As used herein, the term "hydrido" denotes a single hydrogen atom (H). This hydrido group may be attached, for example, to an oxygen atom to form a hydroxyl group; or, as another example, two hydrido groups may be attached to a carbon atom to form a —CH$_2$—group.

As used herein, the term "alkyl" either alone or within other terms such as "phenylalkyl", "naphthalenealkyl" and "alkyloxycarbonyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenoxy, 3-methylbutoxy, 1-methylbutoxy, 1-ethylpropoxy, 2-2-dimethylpropoxy, 1,1-dimethylpropoxy, hexoxy, and 4-methylpentoxy.

As used herein the term "alkenyl" embraces linear or branched unsaturated hydrocarbon radicals having 2 to 6 carbon atoms and containing one carbon to carbon double bond, which carbon to carbon double bond may have either cis or trans geometry within the alkenyl moiety. Illustrative of such groups are ethenyl, propenyl, butenyl, isobutenyl, pentenyl, 3-methyl-1-butenyl, 2-methyl-2-butenyl, 2,3-dimethyl-2-butenyl, and hexenyl.

As used herein the term "alkynyl" embraces linear or branched unsaturated hydrocarbon radicals having 2 to 6 carbon atoms and containing one carbon to carbon triple bond. Illustrative of such radicals are ethynyl, propynyl, butynyl, pentynyl, and hexynyl.

As used herein the term "halo" embraces halogen atoms. Illustrative of such atoms are chloro (Cl), fluoro (F), bromo (Br) and iodo (I).

As used herein, the term "phenylalkylamido" refers to a phenyl moiety which is linked to a amido moiety via an alkyl chain having 1 to 6 carbon atoms with the understanding that the phenyl moiety may be substituted and the alkyl chain may be interrupted by oxygen.

As used herein, the term "5 or 6 carbon membered cyclic ring wherein one or two of the ring carbon atoms are replaced by a hetero atom" refers to a cyclic structure having 5 or 6 ring carbon atoms in which one or two of the ring carbon atoms are replaced by a hetero atom which is selected from nitrogen, oxygen or sulfur. Illustrative of such groups are pyrrolidinyl, pyrrolinyl, pyrrolyl, furanyl, thiophenyl and pyridinyl.

As used herein, the term "alkylsulfonamido" refers to alkyl groups having 1 to 6 carbon atoms bonded to the sulfur of the sulfonamido group. Alkylsulfonamido is represented by the following formula.

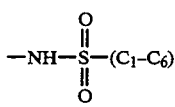

The compounds as shown in Formula I can exist in various isomeric forms and all such isomeric forms are meant to be included. Tautomeric forms are also included as well as pharmaceutically acceptable salts of such isomers and tautomers.

In the structures and formulas herein, the bond drawn across a bond of an aromatic ring can be to any available atom on the aromatic ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, mesylate and tartrate salts. All of these salts may be prepared by conventional means by reacting, for example, the appropriate acid with the corresponding compound of Formula I.

DETAILED DESCRIPTION OF THE INVENTION

The compounds of formula III were prepared in a conventional manner using standard synthetic methods. A general synthetic sequence is outlined in Schemes A and B. The key lefthand portion (formula II) was synthesized by two different routes. Method 1 was employed when Y was a carbon fragment and A was either a carboxylic acid or alcohol. Method 2 was used when Y designates a carboxamide moiety. Thus the halobenzonitrile was coupled to an omega alkynoic acid or an omega alkynoyl alcohol via the Heck reaction employing Tetrakis(triphenylphosphine)-palladium(O) [for related conditions see: H. A. Deck and F. R. Heck *J. Organometallic Chem.* 259–263 (1975)]. Compounds where $Y=CH_2CH_2$ were prepared by a selective hydrogenation using palladium on calcium carbonate. When A was a carboxylic acid group, a modified Curtius reaction [Washburne, S.; Peterson, W. R., *Synthetic Comm.* 2, 227–230 (1972)] converted the carboxylic acid to the corresponding amino compound of formula II. Alternatively, when $R_3$ was an alcohol moiety, the following three step sequence was applied. Mesylation of the alcohol with methanesulfonyl chloride/triethylamine follow by displacement of the mesylate with sodium azide lead to the corresponding azido compound. Reduction of the azide group with triphenylphosphine [Knouzi, N; Vaultier, M.; Carrie, R.; *Bull. Soc. Chim. France,* 815–819 (1985)] provided the desired amino compound of formula II. Finally, when $Y=NHCO$, the appropriate aminobenzonitrile was coupled with N-Boc-$\beta$-alanine using the mixed anhydride method (method 2). Removal of the Boc group with HCl/dioxane again yielded the desired compound of formula II.

Scheme B outlines the general methods used to complete the synthesis of compounds of formula III. The amino compound of formula II was coupled with the appropriate carboxylic acid using standard peptide coupling reagents (e.g. isobutyl chloroformate (IBCF), oxalyl chloride or disuccinimidyl carbonate (DSC)). Generally the carboxylic acid compound is a suitably protected chiral aspartic or glutamic acid. Post coupling modifications to $R_3$ when $R_3=NHCBZ$ could be carried out at this point. Thus, selective hydrogenolysis ($H_2$/Pd/CaCO$_3$) of this material followed by treatment with a suitable acid chloride lead to a series of amide and sulfonamide analogues as described by formula III. The carboxyl protecting group ($R_4=tBu$) was removed under acidic conditions (trifluoroacetic acid), however this procedure could be reserved until the last step of the synthesis. The cyano group was converted to the amidine in three steps: 1) $H_2S$ treatment generated the thioamide, 2) alkylation with methyl iodide lead to the thioimidate and finally 3) treatment of the thioimidate with ammonium acetate yielded the amidine which was generally isolated by precipitation of the zwitterion. Alternatively, purification of the crude product using reverse phase high pressure liquid chromatography provided the desired final product as the trifluoroacetate salt.

The hydroxy acids of formula III ($R_3=OH$) were synthesized (Scheme C, Method 1) by amide formation between the amine (formula II) and the gamma lactone, 5-oxo-2-tetrahydrofurancarboxylic acid, via acid chloride formation with oxalyl chloride. Hydrolysis of the lactone provided a stable hydroxy acid. Conversion of this intermediate to the final product was carried out according to Scheme B. The isomeric hydroxy acid ($R_3=CH_2OH$) was synthesized (Scheme C, Method 2) by coupling the amine (formula II) with tetahydrofuran-3-carboxylic acid, followed by a Ruthenium(VIII) oxidation [Carlsen, P. H. J.; Katsuki, T.; Martin, V.; Sharpless, K. B., *J. Org. Chem.,* 46, 3936–8, (1981)] to yield the lactone. Conversion of the nitrile to the amidine (scheme B) and subsequent base hydrolysis provided the desired product. A pyrrolylsuccinic acid analogue (Scheme C, Method 3) was synthesized by treating aspartic acid-$\beta$-benzyl ester with 2,5-dimethoxytetrahydrofuran. The resulting carboxylic acid was elaborated to the final product according to Scheme B. In addition, various succinic acid analogues may be synthesized by treating a suitably substituted acetic acid methyl ester with LDA followed by alkylation with t-butyl bromoacetate (Scheme C, Method 4). Selective base hydrolysis would provide a monoprotected succinate.

Scheme A

Method 1

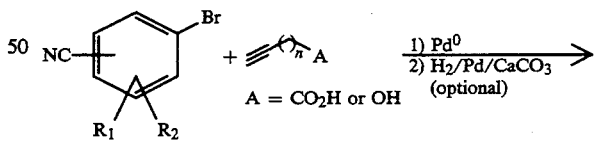

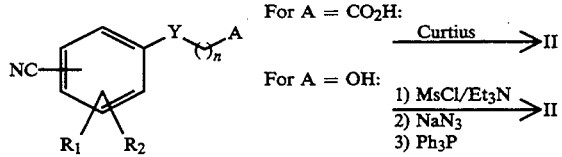

Method 2

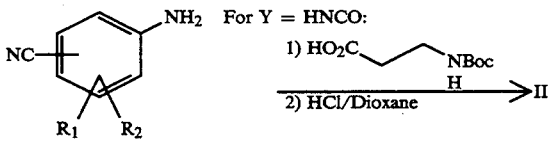

-continued
Scheme A

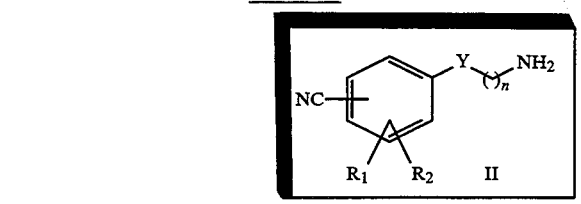

n = p + 2

Scheme B

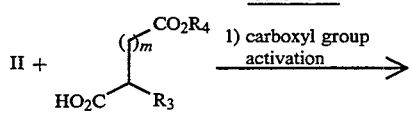

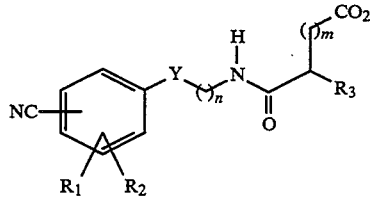

For R3 = NHCBZ/R4 = tBu:
(optional)

1) H2/Pd/CaCO3
2) Acid Chloride/NMM

For R4 = tBu:

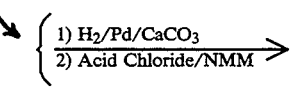

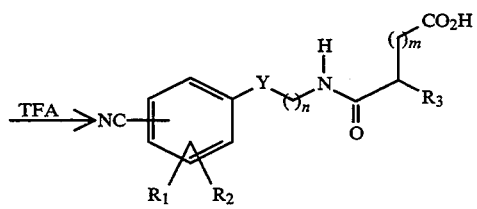

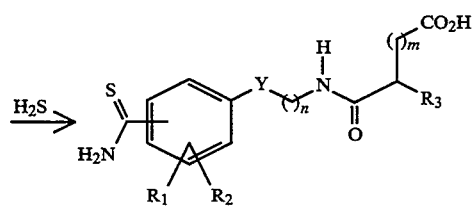

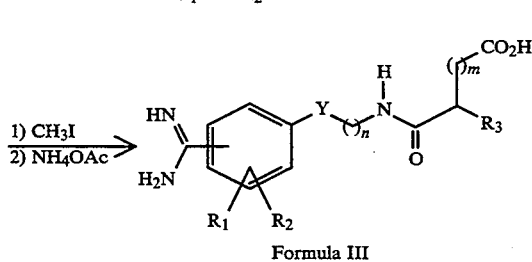

Formula III

Scheme C

Method 1

-continued
Scheme C

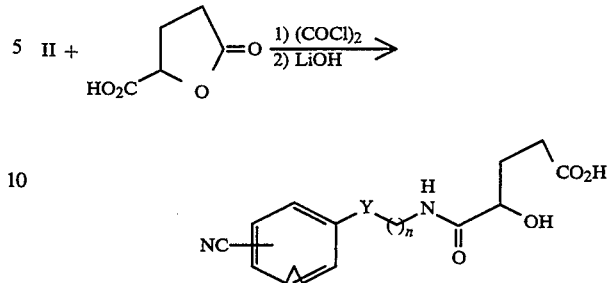

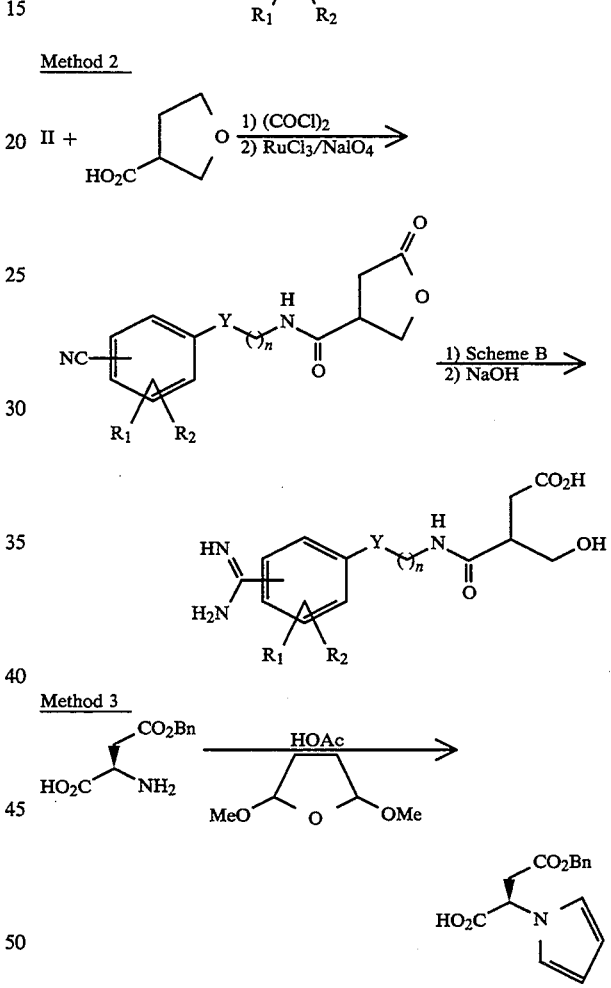

R = alkyl, phenyl, heterocycle

This invention also relates to a method of inhibiting platelet aggregation and more specifically, a method of treatment involving the administration of compounds of Formula I to achieve such inhibition.

For the inhibition of platelet aggregation, compounds of Formula I may be administered orally, parenterally, or by inhalation spray or rectally in dosage unit formulations containing conventional non-toxic pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus dosage regimen may vary widely. Dosage levels of the order from about 0.01 mg to about 150 mg per kilogram of body weight per day are useful in the treatment of the above-indicated conditions (from about 10 mg to about 150 mg per patient per day). For oral administration a daily dose of from about 0.01 to 150 mg/Kg body weight, particularly from about 1 to 30 mg/Kg body weight may be appropriate. For administration by injection a preferred daily dose would be from about 0.01 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention in spirit or scope. In the Examples, all parts are parts by weight and temperature is in degrees Celsius unless otherwise expressly set forth.

EXAMPLE 1

Preparation of 4-[[4-[4-(aminoiminomethyl)phenyl]-butyl]amino]-4-oxo-3(R)-[[(Phenylmethoxy)carbonyl]amino]butanoic acid

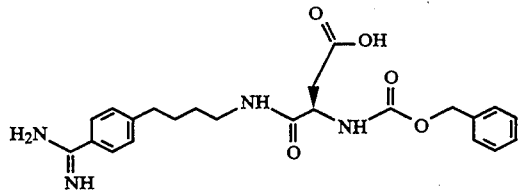

A. Preparation of 5-(4-Cyanophenyl)-4-pentenoic acid

Tetrabutylammonium chloride (hydrate, 17.8 g) was dried by azeotroping with benzene (250 mL round bottom flask equipped with a Dean-Stark apparatus). The benzene was removed in vacuo affording anhydrous tetrabutylammonium chloride (17.0 g, 61.2 mmol). To this flask under argon were added triphenylphosphine (820 mg, 3.13 mmol), palladium acetate (703 mg, 3.13 mmol), 4-bromobenzonitrile (16.9 g, 92.8 mmol), potassium acetate (36.8 g, 375 mmol) and 100 mL of degassed anhydrous dimethylformamide (degassed by bubbling argon through for 10 min., dried over molecular sieves). A solution of 4-pentenoic acid (6.27 g, 62.6 mmol) and degassed anhydrous DMF (35 mL) was then added to the rapidly stirring reaction mixture at 23° C. After 21 hours at 23° C., the reaction mixture was poured slowly into a sodium carbonate solution (3%, 400 mL) and extracted with ethyl acetate (500 mL). The aqueous layer was treated with decolorizing carbon, and filtered. Then, the aqueous layer was acidified to a pH of 2 with 10% HCl which afforded the compound (A) as a white solid (6.82 g, 54%): m.p. 150°–167° C.

An analytical sample was obtained by submitting the sample to further purification by flash chromatography (ethyl acetate:methylene chloride: acetic acid, 1:4:0.05) and recrystallization from ethyl acetate (2 times). The resulting product had the following properties: m.p. 154°–156° C.

Anal. calc'd. for $C_{12}H_{11}NO_2$: C, 71.63; H, 5.51; N, 6.96. Found: C, 71.50; H, 5.54; N, 6.80.

B. Preparation of 5-(4-cyanophenyl)pentanoic acid

A solution of 1.47 g (7.32 mmol) of the product of step A in 90 mL of methanol was hydrogenated over 200 mg of 5% of Pd/CaCO$_3$ at 5 psi hydrogen over a 1.2 h period. After removing the catalyst by filtration and evaporation of the solvent in vacuo, the residue was triturated with ether followed by hexane which afforded a white solid. The resulting product had the following properties: m.p. 101°–102° C.

Anal. calc'd. for $C_{12}H_{13}NO_2$: C, 70.92; H, 6.45; N, 6.89. Found: C, 70.71, H, 6.56; N, 6.87.

C. Preparation of 4-(4-cyanophenyl)butanamine HCl

The product of step B (20.3 g, 0.10 mol) was dissolved in 1,2-dichloroethane (100 mL) and oxalyl chloride (62.5 g, 0.49 mol) was added, followed by DMF (50 μL). The solution was stirred at room temperature until gas evolution ceased (c.a. 30 min). The solvent and excess oxalyl chloride was removed under reduced pressure, redissolved in 200 mL of 1,2-dichloroethane and evaporated under reduced pressure again. The residue was dissolved in dry THF (150 mL) under nitrogen and azidotrimethylsilane (12.7 g, 0.11 mol) was added. After stirring at room temperature for 5 min., the stirred solution was heated in a 70° C. oil bath until gas evolution ceased (c.a. 1 hour). The solution was cooled in an ice bath and concentrated aq. HCl (20 mL) was added all at once and the ice bath was removed. After gas evolution ceased (c.a. 15 min) the solvent was removed under reduced pressure and the residue was partitioned between water and ethyl acetate. The aqueous layer was made basic (250 mL of 1N NaOH) and extracted with ethyl acetate. The organic layer was washed successively with water and sat'd. NaCl, dried (MgSO4), filtered and evaporated under pressure. The residue was redissolved in 150 mL of ethyl acetate and 20 mL of dry 6.9N HCl/dioxone was added with stirring and icebath cooling. The white precipitate was filtered and washed with ethyl acetate then diethyl ether affording 16.9 g (80%) of product: m.p. 155°–160° C.

Anal. calc'd. for $C_{11}H_{15}N_2Cl$: C, 62.70; H, 7.18; N, 13.30; Cl, 16.83. Found: C, 62.76; H, 7.35; N, 13.34; Cl, 16.97.

D. Preparation of 1,1-dimethylethyl 4-[[4-(4-cyanophenyl)butyl]amino]-4-oxo-3(R)-[[(phenylmethoxy)carbonyl]amino]butanoate The product of step C (980 mg, 4.65 mmol) and N-carbobenzyloxy-D-aspartic acid gamma-t-butyl-ester (1.78 g, 5.35 mmol) was suspended in ethyl acetate (25 mL). Neat N-methylpiperidine (500 mg 5.0 mmol) was added followed by solid dicyclohexylcarbodiimide (1.10 g, 5.3 mmol). The suspension was stirred at room temperature overnight, filtered and the filtrate evaporated under reduced pressure. Silica gel chromatography (ethylacetate:hexane, 20:80 followed by ethyl acetate:hexane, 50:50) afforded 1.958 g of product (89%).

Anal. calc'd. for $C_{27}H_{33}N_3O_5$. 0.4EtOAc: C, 66.72; H, 7.09; N, 8.16. Found: C, 66.44; H, 6.97; N, 8.53. $^1$H-NMR (300 MHz, CDCl3) δ1.40 (s, 9H), 1.45–1.70 (m 4H), 2.59 (dd, J=8 Hz, J=16 Hz, 1H), 2.63 (t, J=7 Hz, 2H), 2.97 (dd, J=5 Hz, J=16 Hz, 1H), 3.27 (m, 2H), 4.45 (m, 1H), 5.12 (s, 2H), 5.95 (d, J=9 Hz, 1H, exchangeable), 6.49 (m, 1H, exchangeable), 7.25 (d, J=8 Hz, 2H), 7.30–7.40 (m, 5H), 7.56 (d, J=8 Hz, 2H).

E. Preparation of 4-[[4-[4-(aminoiminomethyl)phenyl]butyl]amino]-4-oxo-3(R)-[[(phenylmethoxy)carbonyl]amino]butanoic acid Hydrogen sulfide was bubbled through a solution of the product of step D (220 mg, 0.46 mmol) in pyridine (5 mL) and triethylamine (0.5 mL) at 23° C. (c.a. 5 min). After 67 hours at 23° C. in an enclosed flask, the reaction mixture was concentrated under reduced pressure. The residue was dissolved in ethyl acetate and washed successively with 1N KHSO4, water, sat'd. sodium chloride, and dried (Na2SO4). Concentration under reduced pressure afforded 250 mg of thioamide. The thioamide was dissolved in acetone (10 mL) and iodomethane (1 mL) and refluxed for 30 min. Concentration under reduced pressure afforded the thioimidate HI (300 mg). To this residue was added anhydrous ammonium acetate (67 mg, 0.87 mmol) and methanol (5 mL). The solution was refluxed for 3 hours under N2 then concentrated under reduced pressure. The residue was dissolved in 90% trifluoroacetic acid/10% water (2 mL), stirred for 1 hour then evaporated under reduced pressure. Reverse phase chromatography on a Waters ® C-18 microbondapak column using an 0.5% acetic acid/water:methanol gradient afforded 83 mg of product.

Anal. calc'd. for $C_{23}H_{28}N_4O_5$. $0.5CF_3CO_2H$, $0.7H_2O$: C, 56.51; H, 5.91; N, 10.98. Found: C, 56.64; N, 5.86; N, 10.81. $^1$H-NMR (300 MHz CD3OD) delta 1.45–1.70 (m, 4H), 2.55–2.82 (m, 4H), 3.20 (t, J=7 Hz, 2H), 4.46 (m, 1H), 5.03–5.15 (m, 2H), 7.24–7.35 (m, 5H), 7.40 (d, J=7 Hz, 2H), 7.70 (d, J=7 Hz, 2H).

EXAMPLE 2

Preparation of 4-[[4-[4-(aminoiminomethyl)phenyl]butyl]amino]-4-oxo-3(R)-[[(4-methylphenylsulfonyl]amino]butanoic acid

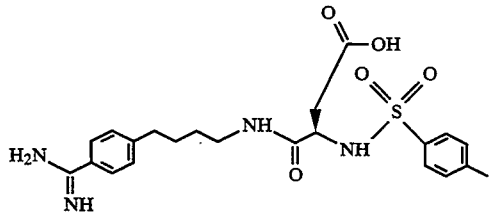

A. Preparation of 1,1-dimethylethyl 4-[[4-(4-cyanophenyl)butyl]amino]-4-oxo-3(R)-aminobutanoate A solution of the product of example 1, step D (3.57 g, 7.4 mmol) dissolved in MeOH (35 mL) and 5% Pd/CaCO3 (200 mg) was hydrogenated at 5 psi of hydrogen over 18 hours. Filtration of the catalyst and removal of the solvent under reduced pressure afforded 2.40 g of product (94%) as an oil which was used directly in the next reaction.

$^1$H-NMR (300 MHz, CD3OD) delta 1.27 (s, 9H), 1.30–1.55 (m, 4H), 2.40 (dd, J=7 Hz, J=18 Hz, 1H), 2.45–2.60 (m, 3H), 3.02 (t, J=7 Hz, 2H) 3.48 (m, 1H), 7.19 (d, J=8 Hz, 2H), 7.42 (d, J=8 Hz, 2H).

B. Preparation of 1,1-dimethylethyl 4-[[4-(4-cyanophenyl)butyl]amino]-4-oxo-3(R)-[[4-methylphenylsufonyl]amino]butanoate To a solution of the product of step A (1.00 g, 2.89 mmol) in pyridine (8 mL) was added p-toluenesulfonyl chloride (830 mg, 4.34 mmol) and stirred at room temperature for 1 hour. The reaction mixture was diluted with water and extracted with ethyl acetate. The organic layer was washed with 1N KHSO4 until the aqueous layer remained acidic, then with brine, dried (Na2SO4), filtered and concentrated under reduced pressure. The residue was filtered through a pad of silica gel (40% ethyl acetate in hexane) affording 1.20 g (83%) of product.

$^{13}$C-NMR (300 MHz, CDCl3) delta 20.84, 27.14, 27.26, 28.10, 34.79, 36.66, 38.56, 52.75, 77.13, 80.98, 108.78, 118.46, 126.48, 128.65, 129.20, 131.43, 136.50, 143.13, 114.37, 169.17, 169.64.

C. Preparation of 4-[[4-[4-(aminoiminomethyl)phenyl]-butyl]amino]-4-oxo-3(R)-[[4-methylphenylsulfonyl]amino]butanoic acid.

The title compound was prepared from the product of step B (1.20 g, 2.40 mmol) in a manner similar to example 1, step E affording 685 mg (62% from nitrile) of product as a white solid (m.p. 170°–172° C. dec.).

Anal. calc'd. for $C_{22}H_{28}N_4O_5S \cdot 1CF_3CO_2H \cdot 0.5H_2O$: C, 49.39; H, 5.18; N, 9.60. Found: C, 49.30; H, 5.02; N, 9.46.

EXAMPLE 3

Preparation of 4-[[4-[4-aminoiminomethyl)phenyl]-butyl]amino]-4-oxo-3R-[(1-oxo-3-phenylpropyl)amino]-butanoic acid

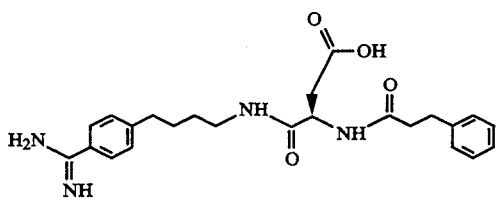

A. Preparation of 1,1-dimethylethyl 4-[[4-(4-cyanophenyl)butyl]amino]-4-oxo-3(R)-[(1-oxo-3-phenylpropyl)amino]butanoate.

The product of example 2, step A (1.43 g, 4.17 mmol) and methylmorpholine (421 mg, 4.17 mmol) was dissolved in 1,2-dichloroethane (20 mL) and cooled in an ice bath. Hydrocinnamoyl chloride (773 mg, 4.59 mmol) in 1,2-dichloroethane (10 mL) was added, warmed to room temperature and stirred for 2 hours. The reaction mixture was partitioned between ethyl acetate and 1N NaHSO$_4$ then washed successively with water, 5% KHCO$_3$, and brine then dried (Na$_2$SO$_4$). Removal of the solvent under reduced pressure afforded 2.00 g (100%) of product as an oil used directly in the next reaction.

Anal. calc'd. for $C_{28}H_{35}N_3O_4$: C, 70.42; H, 7.39; N, 8.80. Found: C, 70.23; H, 7.36; N, 8.62. $^1$H-NMR (300 MHz, CDCl$_3$) delta 1.42 (s, 9H), 1.40–1.65 (m, 4H), 2.40 (dd, J=6 Hz, J=17 Hz, 1H), 2.54 (m, 2H), 2.66 (t, J=7 Hz, 2H), 2.83 (dd, J=4 Hz, J=17 Hz, 1H), 2.96 (m, 2H), 3.18 (m, 2H), 4.67 (m, 1H), 6.35 (m, 1H, exchangeable) 6.75 (d, J=8 Hz, 1H, exchangeable), 7.15–7.31 (m, 7H), 7.56 (d, J=8 Hz, 2H).

B. Preparation of 4-[[4-(4-cyanophenyl)butyl]amino]-4-oxo-3(R)-[(1-oxo-3phenylpropyl)amino]butanoic acid The product of step A (2.00 g, 4.17 mmol) was dissolved in 50 mL of trifluoroacetic acid/water (9:1) and stirred at room temperature for 40 minutes. The solvent was evaporated under reduced pressure and the residue was dissolved in ethyl acetate, washed with water, then extracted (2×) with 10% KHCO$_3$. The combined extracts were acidified to a pH of 1 by the careful addition of solid NaHSO$_4$, extracted with ethyl acetate and dried (Na$_2$SO$_4$). The solvent was removed under reduced pressure and the residue was dissolved in CH$_2$Cl$_2$ (2 mL) then diluted with diethyl ether (50 mL). The gummy precipitate which solidified on standing was filtered and washed with ether affording 1.12 g of product (64%).

Anal. calc'd. for $C_{24}H_{27}N_3O_4 \cdot 0.25H_2O$: C, 67.66; H, 6.39; N, 9.86. Found: C, 67.62; H, 6.38; N, 9.68. $^1$H-NMR (300 MHz, CDCl$_3$) delta 1.38–1.65 (m, 4H), 2.45–2.68 (m, 5H), 2.81 (dd, J=5 Hz, J=16 Hz, 1H), 2.91 (t, J=7 Hz, 2H), 3.16 (m, 2H), 6.73 (t, J=6 Hz, 1H, exchangeable), 7.00 (d, J=7 Hz, 1H, exchangeable), 7.10–7.30 (m, 7H), 7.54 (d, J=8 Hz, 2H).

C. Preparation of 4-[[4-[4-(aminoiminomethyl)phenyl]-butyl]amino]-4-oxo-3R-[(1-oxo-3-phenylpropyl)amino]-butanoic acid Hydrogen sulfide was bubbled through a solution of the product of step B (1.12 g, 2.66 mmol) and triethylamine (1.82 g, 18 mmol) in pyridine (20 mL) at 23° C. (c.a. 10 min.). After stirring for 2.5 days at 23° C. in an enclosed flask the solvent was removed under reduced pressure. The residue was dissolved in ethyl acetate and washed with 1N NaHSO$_4$, dried (Na$_2$SO$_4$) and evaporated under reduced pressure. Trituration of the solid with ether and filtration afforded 1.12 g of yellow thioamide.

Anal. calc'd. for $C_{24}H_{29}N_3O_4S$: C, 63.28; H, 6.42; N, 9.22. Found: C, 62.88, H, 6.50; N, 9.10. This material was dissolved in acetone (25 mL) and iodomethane (4.76 g, 33.6 mmol) was added. The yellow solution was stirred at reflux under nitrogen for 30 min., cooled and evaporated under reduced pressure affording the thioamide . HI. To this residue was added anhydrous ammonium acetate (290 mg, 3.82 mmol) and methanol (15 mL). The solution was refluxed for 3 hours under nitrogen then concentrated under reduced pressure. The oily residue was suspended in 2 mL of water and diluted with 30 mL of acetone. The product slowly precipitated after standing for 3 days. The precipitate was filtered and washed with acetone/water (15:1) then with acetone affording 529 mg of off-white solid (51% from nitrile, m.p. 207°–209° C. dec.).

Anal. calc'd. for $C_{24}H_{30}N_4O_4 \cdot 0.8H_2O$: C, 63.64; H, 7.03; N, 12.37. Found: C, 63.76; H, 6.86; N, 12.30.

EXAMPLE 4

Preparation of 4-[[4-[4-(aminoiminomethyl)phenyl]-butyl]amino]-4-oxo-3(S)-[[(phenylmethoxy)carbonyl]amino]butanoic acid

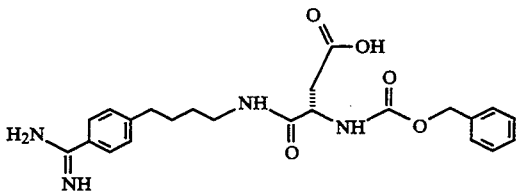

A. Preparation of 1,1-dimethylethyl 4-[[4-(4-cyanophenyl)butyl]amino]-4-oxo-3(S)-[[(phenylmethoxy)carbonyl]amino]butanoate To an ice cooled solution of N-carbobenzyloxy-L-aspartic acid gamma-t-butyl ester (385 mg, 1.19 mmol) in CH$_2$Cl$_2$ (10 mL) was added N-methylmorpholine (120 mg, 1.19 mmol) followed by isobutylchloroformate (163 mg, 1.19 mmol). The solution was stirred at 0° C. for 10 min. then the product of example 1, step C (250 mg, 1.19 mmol) was added followed by an additional 120 mg of N-methylmorpholine. The icebath was removed and the reaction was stirred at room temperature for 3 hours. The reaction mixture was partitioned between ethyl acetate and water, then washed successively with 1N NaHSO$_4$, water, sat'd. NaHCO$_3$ and sat'd. NaCl and dried (Na$_2$SO$_4$). Evaporation under reduced pressure followed by chromatography of the residue (EtOAc/hexane 1:1) afforded 523 mg of product as a colorless oil (92%). $^1$H-NMR (300 MHz, CDCl₃) delta 1.40 (s, 9H), 1.45–1.70 (m, 4H), 2.59 (dd, J=8 Hz, J=16 Hz, 1H), 2.63 (t, J=7 Hz, 2H), 2.97 (dd, J=5 Hz, J=16 Hz), 3.27 (m, 2H), 4.45 (m, 1H), 5.12 (s, 2H), 5.95 (d, J=9 Hz, 1H, exchangeable), 6.49 (m, 1H, exchangeable), 7.25 (d, J=8 Hz, 2H), 7.30–7.40 (m, 5H), 7.56 (d, J=8 Hz, 2H).

B. Preparation of 4-[[4-(4-cyanophenyl)butyl]amino]-4-oxo-4(S)-[[(phenylmethoxy)carbonyl]amino]butanoic acid The product of step A (518 mg, 1.00 mmol) was dissolved in 10 mL of trifluoroacetic acid/water (9:1) and stirred at room temperature for 2 hours. Work up was carried out as described for example 3, step B affording 423 mg of product as a waxy solid (92%). ¹H-NMR (300 MHz, CDCl₃) delta 1.40–1.65 (m, 4H), 2.65 (t, J=8 Hz, 2H), 2.74 (dd, J=8 Hz, J=17 Hz, 1H), 3.01 (dd, J=5 Hz, J=17 Hz, 1H), 3.24 (m, 2H), 4.55 (m, 1H), 5.12 (s, 2H), 6.00 (d, J=9 Hz, 1H, exchangeable), 6.65 (m, 1H, exchangeable), 7.25 (d, J=8 Hz, 2H), 7.30–7.40 (m, 5H), 7.55 (d, J=8 Hz, 2H).

C. Preparation of 4-[[4-[4-(aminoiminomethyl)phenyl]butyl]amino]-4-oxo-3(S)-[[(phenylmethoxy)carbonyl]amino]butanoic acid.

The title compound was prepared from the product of step B (404 mg, 0.954 mmol) in a manner similar to example 3, step C. The product was precipitated as the zwitterion with water/acetone (1:15) affording 165 mg of white solid (39% from nitrile, m.p. 138°–141° C. dec.).

Anal. calc'd. for $C_{23}H_{28}N_4O_5 \cdot 0.8H_2O$: C, 60.72; H, 6.56; H, 12.32. Found: C, 60.55; H, 6.26; N, 12.20.

EXAMPLE 5

Preparation of 5-[[4-[4-(aminoiminomethyl)phenyl]butyl]amino]-5-oxo-4(R)-[[(phenylmethoxy)carbonyl]amino]pentanoic acid

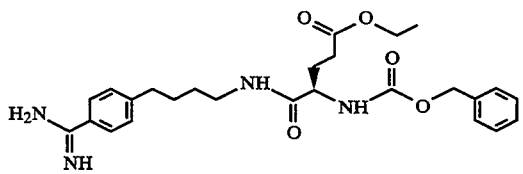

A. Preparation of 1-dimethylethyl 5-[[4-(4-cyanophenyl)butyl]amino]-5-oxo-4(R)-[[(phenylmethoxy)carbonyl]amino]pentanoate The title compound was prepared in a manner similar to example 4, step A substituting carbobenzyloxy-D-glutamic acid gamma-t-butyl ester (7.59 g, 22.5 mmol) for the aspartic acid derivative. The product (10.80 g) was obtained as a colorless oil which solidified on standing (97%).

Anal. calc'd. for $C_{28}H_{35}N_3O_5$: C, 68.13; H, 7.15; N, 8.51. Found: C, 67.96; H, 7.24; N, 8.46.

B. Preparation of 5-[[4-(4-cyanophenyl)butyl]amino]-5-oxo-4(R)-[[(phenylmethoxy)carbonyl]amino]pentanoic acid The title compound was prepared from the product of step A (2.00 g, 4.05 mmol) in a manner similar to example 4, step B affording 1.58 g (89%) of off-white solid (m.p. 126.5°–129.5° C.).

Anal. calc'd. for $C_{24}H_{27}N_3O_5$: C, 65.89; H, 6.22; N, 9.61. Found: C, 65.83; H, 6.28; N, 9.61. ¹H-NMR (300 MHz, CDCl₃) delta 1.40–1.70 (m, 4H), 1.80–2.15 (m, 2H), 2.30–2.60 (m, 2H), 2.65 (t, J=7 Hz, 2H), 3.25 (m, 2H), 4.30 (m, 1H), 5.08 (s, 2H), 5.81 (d, J=9 Hz, 1H, exchangeable), 6.75 (m, 1H), 7.24 (d, J=8 Hz, 2H), 7.25–7.40 (m, 5H), 7.54 (d, J=8 Hz, 2H).

C. Preparation of 5-[[4-[4-(aminoiminomethyl)phenyl]butyl]amino]-5-oxo-4(R)-[[(phenylmethoxy)carbonyl]amino]pentanoic acid.

The title compound was prepared from the product of step B (1.52 g, 3.36 mmol) in a manner similar to example 3, step C affording 990 mg (65%) of off-white solid (m.p. 241°–243° C. dec.).

Anal. calc'd. for $C_{24}H_{30}N_4O_5$: C, 63.42; H, 6.65; N, 12.33. Found: C, 63.11; H, 6.77; N, 11.96.

EXAMPLE 6

Preparation of Ethyl 5-[[4-[4-(aminoiminomethyl)phenyl]butyl]amino]-5-oxo-4(R)[[(phenylmethoxy)carbonyl]amino]pentanoate.

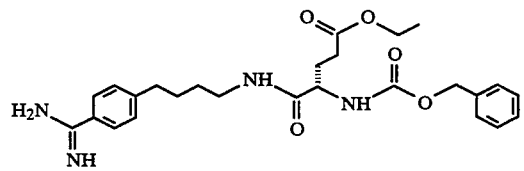

The product of example 5, step C (986 mg, 2.17 mmol) was dissolved in a solution of sat'd. HCl in EtOH (35 mL) and stirred at room temperature overnite. The solvent was removed under reduced pressure to dryness. The gummy material was dissolved in a minimal volume of CH₂Cl₂ and precipitated by the addition of ether leaving a gummy product upon decantation of the solvent. Reprecipitation from CH₂Cl₂/ether, decantation and drying under vacuum afforded a hygroscopic foam (1.07 g, 95.5%).

Anal. calc'd. for $C_{26}H_{35}N_4O_5Cl \cdot 0.75H_2O$: C, 58.64; H, 6.91; N, 10.52. Found: C, 58.68; H, 6.78; N, 10.33. ¹H-NMR (300 MHz, CD₃OD) δ1.22 (t, J=7 Hz, 3H), 1.45–1.75 (m, 4H), 1.80–2.12 (m, 2H), 2.39 (t, J=7 Hz, 2H), 2.74 (t, J=6 Hz, 2H), 3.22 (t, J=7 Hz, 2H), 4.03–4.15 (m, 3H), 5.01–5.12 (m, 2H), 7.25–7.38 (m, 5H), 7.45 (d, J=8 Hz, 2H), 7.71 (d, J=8 Hz, 2H), 8.68 (s, 1H), 9.19 (s, 1H).

EXAMPLE 7

Preparation of 5-[[4-[4-(aminoiminomethyl)phenyl]butyl]amino]-5-oxo-4(S)-[[(phenylmethoxy(carbonyl)amino]pentanoic acid

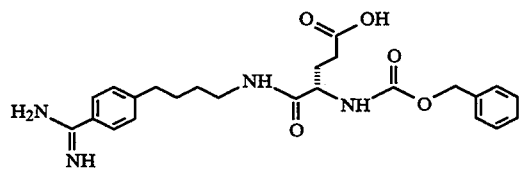

A. Preparation of 1,1-dimethylethyl 5-[[4-(4-cyanophenyl)butyl]amino]-5-oxo-4(S)-[[(phenylmethoxy)carbonyl]amino]pentanoate.

The title compound was prepared in a manner similar to example 4, step A substituting N-carbobenzyloxy-L-glutamic acid gamma-t-butyl ester (410 mg, 1.19 mmol) for the aspartic acid derivative. The product (538 mg) was obtained as a colorless oil (92%). ¹H-NMR (300 MHz, CDCl₃) delta 1.44 (s, 9H), 1.45–1.68 (m, 4H), 1.82–2.11 (m, 2H), 2.21–250 (m, 2H), 2.67 (t, J=7 Hz, 2H), 3.26 (m, 2H), 4.15 (m, 1H), 5.10 (s, 2H), 5.67 (d, J=7 Hz, 1H, exchangeable), 6.33 (m, 1H, exchangeable), 7.25 (d, J=8 Hz, 2H), 7.30–7.40 (m, 5H), 7.55 (d, J=8 Hz, 2H).

B. Preparation of 5-[[4-(4-cyanophenyl)butyl]amino]-5-oxo-4(S)-[[(phenylmethoxy)carbonyl]amino]pentanoic acid The title compound was prepared from the product of step A (470 mg, 0.95 mmol) in a manner similar to example 4, step B affording 315 mg (76%) of white solid. $^1$H-NMR (300 MHz, CDCl$_3$/1drop CD$_3$OD) delta 1.40–1.70 (m, 4H), 1.80–2.15 (m, 2H), 2.30–2.60 (m, 2H), 2.65 (t, J=7 Hz, 2H), 3.25 (m, 2H), 4.20 (m, 1H), 5.09 (s, 2H), 5.90 (d, J=8 Hz, 1H, exchangeable), 6.80 (m, 1H, exchangeable), 7.24 (d, J=8 Hz, 2H), 7.25–7.40 (m, 5H), 7.54 (d, J=8 Hz, 2H).

C. Preparation of 5-[[4-[4-(aminoiminomethyl)phenyl]butyl]amino]-5-oxo-4(S)-[[(phenylmethoxy)carbonyl]amino]pentanoic acid The title compound was prepared from the product of step B (250 mg, 0.57 mmol) in a manner similar to example 3, step C affording 146 mg (56%) of off-white solid (m.p. 241°–243° C. dec.).

Anal. calc'd. for C$_{24}$H$_{30}$N$_4$O$_5$: C, 63.42; H, 6.65; N, 12.33. Found: C, 62.98; H, 6.65; N, 12.17.

EXAMPLE 8

Preparation of 5-[[4-[4-(aminoiminomethyl)phenyl]butyl]amino]-5-oxo-4(R)-methylsulfonylaminopentanoic acid

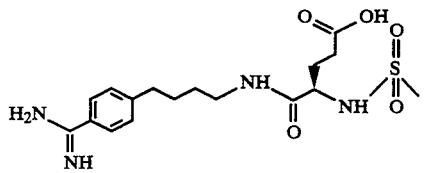

A. Preparation of 5-[[4-(4-cyanophenyl)butyl]amino]-5-oxo-4(R)-methylsulfonylaminopentanoic acid.

The product of example 5, step A (500 mg, 1.01 mmol) was dissolved in EtOAc (15 mL) followed by 5% Pd/CaCO$_3$ (200 mg). The reaction was stirred over a balloon of hydrogen overnite. The balloon was removed and N-methylmorpholine (153 mg, 1.52 mmol) was added followed by methanesulfonyl chloride (174 mg, 1.52 mmol). The reaction was stirred overnite at room temperature, filtered through a pad of celite and the filtrate was washed successively with 1N NaHSO$_4$, sat'd. NaHCO$_3$ and dried MgSO$_4$). Removal of the solvent under reduced pressure afforded a gummy residue which was dissolved in 10 mL of trifluoroacetic acid/water (9:1) and stirred at room temperature for 30 minutes. The solvent was removed under reduced pressure, the residue dissolved in a minimal amount of dichloromethane and the product precipitated by the addition of Et$_2$O. The white solid was filtered and washed with Et$_2$O affording 360 mg (93%) of product.

Anal. calc'd. for C$_{17}$H$_{23}$N$_3$O$_5$S. 0.5H$_2$O: C, 52.29; H, 6.20; N, 10.76. Found: C, 52.48; H, 6.15; N, 10.37. $^1$H-NMR (300 MHz, CDCl$_3$/CD$_3$OD) δ1.40–1.72 (m, 4H), 1.75–2.10 (m, 2H), 2.40–2.65 (m, 2H), 2.70 (t, J=8 Hz, 2H), 2.91 (s, 3H), 3.27 (m, 2H), 3.92 (m, 1H), 7.28 (d, J=8 Hz, 2H), 7.58 (d, J=8 Hz, 2H).

B. Preparation of 5-[[4-[4-(aminoiminomethyl)phenyl]butyl]amino]-5-oxo-4(R)-methylsulfonylaminopentanoic acid The title compound was prepared from the product of step A (560 mg, 1.47 mmol) in a manner similar to example 3, step C affording 396 mg (68%) of an off-white solid (m.p. 208°–212° C. dec.).

Anal. calc'd. for C$_{17}$H$_{26}$N$_4$O$_5$S. 0.9H$_2$O: C, 49.24; H, 6.76; N, 13.51. Found: C, 49.34; H, 6.33; N, 13.18.

EXAMPLE 9

Preparation of Ethyl 5-[[4-(4-aminoiminomethyl)phenyl]butyl]amino]-5-oxo-4(R)-methylsulfonylaminopentanoate, monohydrochloride

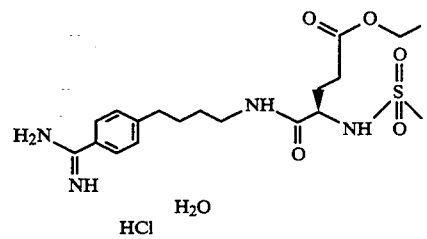

The product of example 8, step B (640 mg, 1.61 mmol) was dissolved in 20 mL of sat'd. HCl/ethanol and stirred at room temperature overnite. The solvent was removed and the gummy residue was triturated with acetonitrile and decanted. The residue was evaporated to dryness from ethanol/ether affording the product (680 mg, 91%) as a hygroscopic foam.

Anal. calc'd. for C$_{19}$H$_{31}$N$_4$O$_5$SCl. 1H$_2$O: C, 47.14; H, 6.92; N, 11.65. Found: C, 47.53; H, 7.10; N, 11.61. $^1$H-NMR (300 MHz, CD$_3$OD) δ1.24 (t, J=7 Hz, 3H), 1.50–1.77 (m, 4H), 1.80–2.10 (m, 2H), 2.45 (t, J=7 Hz, 2H), 2.76 (t, J=7 Hz, 2H), 2.91 (s, 3H), 3.25 (t, J=7 Hz, 2H), 3.89 (m, 1H), 4.13 (q, J=7 Hz, 2H), 7.47 (d, J=8 Hz, 2H), 7.72 (d, J=8 Hz, 2H).

EXAMPLE 10

Preparation of 5-[[4-[4-aminoiminomethyl)phenyl]butyl]amino]-5-oxo-4(R)-[[(1-oxo-3-phenyl)propyl]amino]pentanoic acid

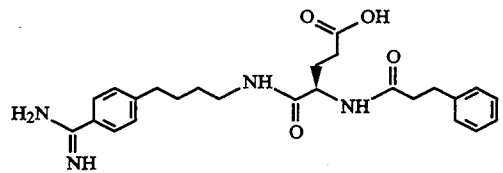

A. Preparation of 5-[[4-(4-cyanphenyl)butyl]amino]-5-oxo-4(R)-[[(1-oxo-3-phenyl)propyl]amino]pentanoic acid The title compound was prepared from the product of example 5, step A (2.00 g, 4.06 mmol) in a manner similar to example 8, step A substituting hydrocinnamoyl chloride for methanesulfonyl chloride. The product was obtained from methylene chloride/diisopropyl ether affording 1.66 g (94%) as a white solid (m.p. 119°–122° C.).

Anal. calc'd. for C$_{25}$H$_{29}$N$_3$O$_4$. 0.6H$_2$O: C, 67.27; H, 6.82; N, 9.42. Found: C, 67.23; H, 6.68; N, 9.27.

B. Preparation of 5-[[4-[4-aminoiminomethyl)phenyl]butyl]amino]-5-oxo-4(R)-[[(3-phenyl-1-oxo)propyl]amino]pentanoic acid The title compound was prepared from the product of step A (1.61 g, 3.70 mmol) in a manner similar to example 3, step C affording 1.08 g (63%) of white solid [(m.p. 242°–243° C. dec. (acetone/water)].

Anal. calc'd. for C25H32N4O4. 0.5H2O: C, 65.05; H, 7.21; N, 12.14. Found: C, 64.96, H, 7.16; N, 11.94.

EXAMPLE 11

Preparation of 5-[[4-[4-(aminoiminomethyl)phenyl]-pent-4-ynyl]amino]-5-oxo-4(R)-[[(phenylmethoxy)carbonyl]aminopentanoic acid

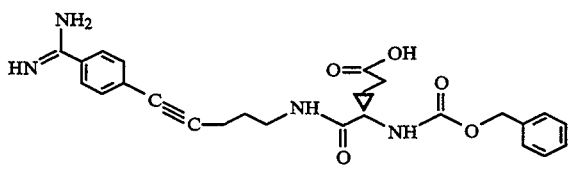

A. Preparation of 5-(4-cyanophenyl]4-pentynol

To a solution of 4-bromobenzonitrile (105.0 g, 0.577 mol) and triethylamine (108.1 g, 1.07 mol) in 900 mL of acetonitrile under nitrogen was added 4-pentynol (50 g, 0.594 mol) dissolved in acetonitrile followed by tetrakis (triphenylphosphine) palladium (5.00 g, 3.23 mmol). The reaction flask was wrapped in aluminum foil and the mixture was refluxed for 20 hours, cooled to room temperature and filtered. The filtercake was washed with acetonitrile and the filtrate was evaporated under reduced pressure. The residue was dissolved in ethyl acetate and washed successively with water, 5% aq. HCl, water, 5% aq. potassium bicarbonate, water, and brine. The organic layer was dried MgSO4) and the solvent removed under reduced pressure. The residue was dissolved in 1.8 L of diethyl ether, treated with Darco, filtered and the filtrate reduced to a volume of 550 mL on a steam bath. A solid yellow precipitate formed upon cooling to −30° C. The solid was filtered and washed with cold diethyl ether and dried affording 72.90 g of product (m.p. 76°-83° C.). The filtrate was concentrated under reduced pressure and chromatographed (ethyl acetate:hexane, 1:1) affording 10.2 g of product after recrystallization from diethyl ether (m.p. 81°-84° C., 78% combined yield).

Anal. calc'd. for C12H11NO: 6, 77.82; H, 5.99; N, 7.56. Found: C, 77.30; H, 6.08; N, 7.38.

B. Preparation of 5-(4-cyanophenyl)-4-pentynyl methanesulfonate

To a solution of the product of step A (10.00 g, 54.0 mmol) and triethylamine (5.73 g, 56.7 mmol) in 80 mL of methylene chloride was added methanesulfonyl chloride (6.61 g, 56.7 mmol) at room temperature. The reaction mixture was allowed to reach reflux and stirred for 1 hour. The solvent was removed under reduced pressure and partitioned between water and ethyl acetate. The organic phase was washed successively with 5% NaHSO4, 10% KHCO3 and brine and dried (Na2SO4). Evaporation under reduced pressure afforded 13.4 g (94%) of yellow solid.

1H-NMR (300 MHz, CDCl3) δ2.07 (p, J=6 Hz, 2H), 2.63 (t, J=6 Hz, 2H), 3.05 (s, 3H), 4.40 (t, J=6 Hz, 2H), 7.47 (d, J=8 Hz, 2H), 7.60 (d, J=8 Hz, 2H).

C. Preparation of 1-(4-cyanophenyl)-5-azido-1-pentyne

To a solution of the product of step B (13.40 g, 50.9 mmol) in dimethylformamide (35 mL) was added NaN3 (16.5 g, 255 mmol). The reaction was stirred at room temperature for 18 hours then at 60° C. for 2 hours, cooled to room temperature, diluted with water (400 mL) and extracted with ethyl acetate. The organic layer was washed with water (2×) then with brine and dried (Na2SO4). Evaporation under reduced pressure afforded 10.70 g (100%) of product as a tan oil.

1H-NMR (200 MHz, CDCl3) δ1.89 (p, J=6 Hz, 2H), 2.57 (t, J=6 Hz, 2H), 3.48 (t, J=6 Hz, 2H), 7.45 (d, J=8 Hz, 2H), 7.58 (d, J=8 Hz, 2H).

D. Preparation of 5-(4-cyanophenyl)-4-pentynamine hydrochloride

To a solution of the product of step C (10.46 g, 49.8 mmol) and water (1.35 mL, 74.7 mmol) in tetrahydrofuran (100 mL) was added triphenylphosphine (14.4 g, 54.9 mmol). The reaction mixture was stirred at room temperature for 17 hours and evaporated under reduced pressure. The residue was dissolved in ethyl acetate and filtered. To the ice cooled filtrate was added 6.9N HCl/dioxane. The precipitate was filtered and washed with ethyl acetate then ether. Recrystallization of the product from isopropyl alcohol afforded 7.00 g (64%) of light yellow solid (m.p. 202°-205° C.).

Anal. calc'd. for C12H13N2Cl: C, 65.31: H, 5.94; N, 12.69; Cl, 16.06 Found: C, 65.06; H, 6.00; N, 12.58; Cl, 16.02.

E. Preparation of 1,1-dimethylethyl 5-[[5-(4-cyanophenyl)pent-4-ynyl]amino]5-oxo-4(R)-[[(phenylmethoxy)carbonyl]amino]pentanoate.

The title compound was prepared from the product of step D (756 mg, 2.27 mmol) in a manner similar to example 5, step A affording 875 mg (90%) of product as a white solid (m.p. 78°-79° C).

Anal. calc'd. for C29H33N3O5: C, 69.17; H, 6.60; N, 8.34. Found: C, 68.93: H, 6.67; N, 8.26.

F. Preparation of 5-[[5-(4-cyanophenyl)pent-4-ynyl]amino]-5-oxo-4(R)-[[(phenylmethoxy)carbonyl]amino]pentanoic acid The title compound was prepared from the product of step E (1.01 g, 2.00 mmol) in a manner similar to example 5, step B affording 750 mg (84%) of product as a white solid (m.p. 92°-96° C.).

Anal. calc'd. for C25H25N3O5.0.3H2O: C, 62.22; H, 5.70; N, 9.27. Found: C, 66.19; H, 5.62; N, 9.26.

G. Preparation of 5-[[4-[4-(aminoiminomethyl)phenyl]-pent-4-ynyl]amino]-5-oxo-4(R)-[[(phenylmethoxy) carbonyl]aminopentanoic acid.

The title compound was prepared from the product of step F (730 mg, 1.63 mmol) in a manner similar to example 3, step C affording 374 mg (49%) of product as an off-white solid (m.p. 192°-193° C., dec.).

Anal. calc'd. for C25H28N4O5. 1H2O: C, 62.22; H, 6.27; N, 11.61. Found: C, 62.24; H, 5.96; N, 11.55.

EXAMPLE 12

Preparation of 5-[[3-[4-(aminoiminomethyl)phenyl]-propyl]amino]-5-oxo-4(R)-[[(phenylmethoxy)carbonyl]amino]pentanoic acid

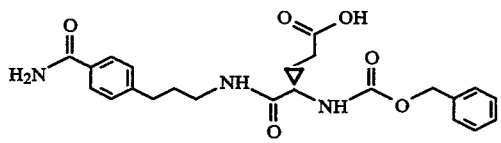

A. Preparation of 3-(4-cyanophenyl)propyl methanesulfonate

To a solution of 3-(4-cyanophenyl)propanol (2.32 g, 13.2 mmol) and triethylamine (1.40 g, 13.9 mmol) in methylene chloride (20 mL) was added methanesulfonyl chloride (1.59 g, 13.9 mmol). The reaction mixture was stirred at room temperature for 1 hour, diluted with ethyl acetate, washed successively with 1N NaHSO₄, 10% NaHCO₃ and dried (MgSO₄). Evaporation under reduced pressure afforded 2.56 g (77%) of product.

¹H-NMR (300 MHz, CDCl₃) δ2.10 (m, 2H), 2.83 (t, J=7 Hz, 2H), 3.02 (s, 3H), 4.24 (t, J=7 Hz, 2H), 7.32 (d, J=8 Hz, 2H), 7.60 (d, J=8 Hz, 2H).

B. Preparation of 3-(4-cyanophenyl)-1-azidopropane

To a solution of the product of step A (2.23 g, 8.81 mmol) in dimethylformamide (6 mL) was added sodium azide (2.86 g, 44 mmol). The reaction was stirred at 50° C. for 18 hours, cooled to room temperature, diluted with water (200 mL) and extracted with ethyl acetate (2×). The organic layer was washed with water and dried MgSO₄). Evaporation of the solvent under reduced pressure afforded 1.54 g (94%) of product.

¹H-NMR (300 MHz, CDCl₃) δ1.92 (m, 2H), 2.79 (t, J=7 Hz, 2H), 3.31 (t, J=7 Hz, 2H), 7.30 (d, J=8 Hz, 2H), 7.60 (d, J=8 Hz, 2H).

C. Preparation of 3-(4-cyanophenyl)propanamine hydrochloride

To a solution of the product of step B (1.54 g, 9.17 mmol) in methanol (20 mL) was added 5% Pd/CaCO₃ (250 mg) and hydrogenated under a balloon of hydrogen for 18 hours. The catalyst was removed and the solvent evaporated under reduced pressure. The residue was dissolved in ethyl acetate and 6N HCl/dioxane (c.a. 2 mL) was added resulting in a white precipitate. The product was filtered and washed with ethyl acetate affording 1.36 g (75%) of product.

Anal. calc'd. for C₁₀H₁₂N₂Cl. 0.1H₂O: C, 60.51; H, 6.70; N, 14.11. Found: C, 60.72; H, 6.75; N, 13.93. ¹H-NMR (300 MHz, CDCl₃OD) δ1.99 (m, 2H), 2.81 (t, J=7 Hz, 2H), 2.96 (t, J=7 Hz, 2H), 7.45 (d, J=8 Hz, 2H), 7.68 (d, J=8 Hz, 2H).

D. Preparation of 1,1-dimethylethyl 5-[[3-(4-cyanophenyl)propyl]amino]-5-oxo-4(R)-[[(phenylmethoxy)carbonyl]amino]pentanoate.

The title compound was prepared from the product of step C (520 mg, 1.54 mmol) in a manner similar to example 5, step A affording 660 mg (89%) of product as an oil which solidified on standing.

¹H-NMR (300 MHZ, CDCl₃) δ1.91 (s, 9H), 1.83 (p, J=7 Hz, 2H), 1.90–2.12 (m, 2H), 2.24–2.52 (m, 2H), 2.67 (t, J=7 Hz, 2H), 3.27 (m, 2H), 4.15 (m, 2H), 5.10 (s, 2H), 5.68 (d, J=8 Hz, 1H, exchangeable), 6.42 (m, 1H, exchangeable), 6.42 (m, , exchangeable), 7.27 (d, J=8 Hz, 2H), 7.33 (m, 5H), 7.57 (d, J=8 Hz, 2H).

E. Preparation of 5-[[3-(4-cyanophenyl)propyl]amino]-5-oxo-4(R)-[[(phenylmethoxy)carbonyl]amino]pentanoic acid.

The title compound was prepared from the product of step D (650 mg, 1.36 mmol) in a manner similar to example 5, step B affording 505 mg (88%) of product as a white solid.

Anal. calc'd. for C₂₃H₂₅N₃O₅. 0.3H₂O: C, 64.33; H, 6.02; N, 9.79. Found: C, 64.33; H, 5.95; N, 9.74. ¹H-NMR (300 MHz, CDCl₃/2 drops CD₃OD) δ1.75–2.12 (m, 4H), 2.30–2.60 (m, 2H), 2.68 (t, J=7 Hz, 2H), 3.25 (m, 2H), 4.17 (m, 1H), 5.10 (s, 2H), 7.28 (d, J=8 Hz, 2H), 7.32 (m, 2H), 7.57 (d, J=8 Hz, 2H).

F. Preparation of 5-[[3-(4-aminoiminomethyl)phenyl]propyl]amino]-5-oxo-4(R)-[[(phenylmethoxy]carbonyl]amino]pentanoic acid.

The title compound was prepared from the product of step E (485 mg, 1.15 mmol) in a manner similar to example 3, step C affording 310 mg (61%) of product as an off-white solid (m.p. 243°–245° C. dec.).

Anal. calc'd. for C₂₃H₂₈N₄O₅. 0.25H₂O: C, 62.08; H, 6.46; N, 12.59. Found: C, 62.14; H, 6.37; N, 12.32.

EXAMPLE 13

Preparation of 5-[[4-[4-(aminoiminomethyl)phenyl]butyl]amino]-5-oxo-4(R)-hydroxypentanoic acid A. Preparation of 2(R)-4-[[4-(cyanophenyl)butyl]aminocarbonyl]-5-oxo-tetrahydrofuran To a solution of 5-oxo-2(R)-tetrahydrofurancarboxylic acid (1.00 g, 7.69 mmol) in 1,2-dichlorethane (15 mL) was added oxalyl chloride (4.87 g, 38.5 mmol) and DMF (2 μL). The reaction was stirred at room temperature until gas evolution ceased (c.a. 30 min) then evaporated under reduced pressure. The residue was redissolved in 1,2-dichlorethane (15 mL) and concentrated under reduced pressure again. The resulting acid chloride was dissolved in dichloromethane (15 mL) and cooled to −70° C. under N₂. To this solution was added the product of example 1 step C (1.62 g, 7.69 mmol) as a dry powder followed by N-methylmorpholine (1.55 g, 15 mmol). The cooling bath was removed and the reaction was stirred at ambient temperature for 2 hours. The solvent was removed under reduced pressure and the residue was partitioned between water and ethyl acetate. The organic layer was washed successively with water, 10% NaHSO₄, 10% K₂CO₃ and brine and dried (Na₂SO₄). Removal of the solvent under reduced pressure afforded 2.06 g (94%) of product as a tan solid.

Anal. calc'd. for C₁₆H₁₈N₂O₃: C, 67.12; H, 6.34; N, 9.78. Found: C, 66.79; H, 6.38; N, 9.67. ¹H-NMR (300 MHz, CDCl₃) δ1.50:1.72 (m, 4H), 2.27–2.40 (m, 1H), 2.54–2.76 (m, 5H), 3.21–3.44 (m, 2H), 6.84 (t, J=7 Hz, 2H), 6.39 (br.s, 1H, exchangeable), 7.28 (d, J=8 Hz, 2H), 7.59 (d, J=8 Hz, 2H).

B. Preparation of 4-[[-(cyanophenyl)butyl]amino]-5-oxo-4(R)-hydroxypentanoic acid To a solution of the product of step A (3.00 g, 10.5 mmol) in dioxane (40 mL) and water (10 mL) was added LiOH.H₂O (487 mg, 11.6 mol). The reaction was stirred at room temperature for 17 hours then concentrated under reduced pressure to remove most of the dioxane. The reaction was diluted with water, washed with Et₂O and acidified to a pH of 1 with 2N HCl (8 mL). The aqueous phase was extracted (2×) with ethyl acetate, dried (MgSO₄) and evaporated under reduced pressure affording 3.20 g (100%) of gummy product used directly in the next reaction.

¹H-NMR (300 MHz, CDCl₃) δ1.45–1.72 (m, 4H), 1.94 (h, J=7H, 1H), 2.10–2.23 (m, 1H), 2.40–2.63 (m, 2H), 2.70 (t, J=7 Hz, 2H), 3.30 (m, 2H), 4.21 (m, 1H), 6.95 (t, J=7 Hz, 1H, exchangeable), 7.28 (d, J=8 Hz, 2H), 7.57 (d, J=8 Hz, 2H).

C. Preparation of 5-[[4-[-(aminoiminomethyl)phenyl]butyl]amino]-5-oxo-4(R)-hydroxypentanoic acid The title compound was prepared from the product of step B (3.20 g, 10.5 mmol) in a manner similar to example 3, step C affording 2.35 g (70%) of product as an off-white solid (m.p. 238°–239.5° C. dec.).

Anal. calc'd. for $C_{16}H_{23}N_3O_4 \cdot 0.25N_2O$: C, 58.97; H, 7.42; N, 12.89. Found: C, 58.64; H, 7.24; N, 12.71.

EXAMPLE 14

Preparation of 2(R)-[[4-4-(aminoiminomethyl)phenyl]butyl]aminocarbonyl]-5-oxo-tetrahydrofuran trifluoroacetate

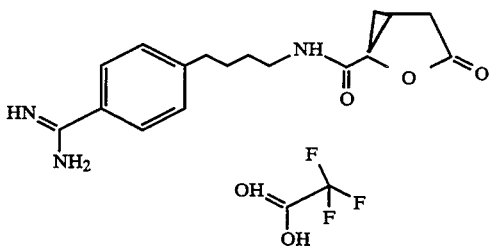

To a suspension of the product of example 13, step C (2.00 g, 6.23 mmol) in dichloromethane (35 mL) was added trifluoroacetic acid (3.35 mL). The resulting solution was stirred at room temperature for 4 hours. The solvent was removed under reduced pressure and the residue was dissolved in dichloromethane (20 mL) then diluted with ether (c.a. 70 mL). The white precipitate was filtered, washed with ether and dried affording 2.46 g (95%) of product (m.p. 227°–228° C. dec.).

Anal. calc'd. for $C_{18}H_{22}N_3O_5F_3$: C, 51.80; H, 5.31; N, 10.07. Found: C, 51.43; H, 5.24; N, 9.87.

EXAMPLE 15

Preparation of 4-[[4-[4-aminoiminomethyl)phenyl]butyl]amino]-4-oxo-3R-(1H-pyrrol-1-yl)butanoic acid, monohydroiodide

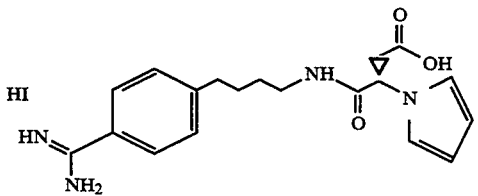

A. Preparation of 4-oxo-4-phenylmethoxy-2(R)-(1-pyrrol)butanoic acid

To a suspension of D-aspartic acid beta benzyl ester (2.00 g, 8.96 mmol) in acetic acid (6 mL) was added 2,5-dimethoxytetrahydrofuran (1.18 g, 8.96 mmol). The reaction was stirred at 80° C. for 1 hour and then the solvent was removed under reduced pressure. The residue was taken up in ether and washed successively with water and sat'd NaCl. The organic layer was extracted (2×) with 5% NaHCO₃. The combined aqueous extract was acidified to a pH of 1 (solid NaHSO₄) and extracted with ether. The ether layer was dried (Na₂SO₄) and concentrated under reduced pressure affording 760 mg of product (31%) as a thick oil.

¹H NMR (300 MHz, CDCl₃) δ3.02 (dd, J=7 Hz, J=16 Hz, 1H), 3.29 (dd, J=7 Hz, J=16 Hz, 1H), 5.11 (s, 2H), 5.17 (t, J=7 Hz, 1H), 6.18 (t, J=2 Hz, 2H), 6.70 (t,J=2 Hz, 2H), 7.20–7.40 (m, 5H).

B. Preparation of phenylmethyl 4-[[4(4-cyanophenyl)butyl]amino]-4-oxo-3(R)- (1-pyrrolyl)butanoate The title compound was prepared from the product of step A (461 mg, 1.69 mmol) in a manner similar to example 4, step A. The product (613 mg) was obtained after chromatography (ethyl acetate/hexane 1:1) as a light brown oil (84%).

¹H-NMR (300 MHz, CDCl₃) δ1.30–1.60 (m, 4H), 2.63 (t, J=7 Hz, 2H), 2.97 (dd, J=8 Hz, J=16 Hz, 1H), 3.10–3.25 (m, 2H), 3.45 (dd, J=6 Hz, J=16 Hz, 1H), 5.00–5.15 (m, 3H), 5.32 (s, 1H exchangeable), 6.23 (t, J=2 Hz, 2H), 6.68 (t, J=2 Hz, 2H), 7.15–7.40 (m, 7H), 7.56 (d, J=8 Hz, 2H).

C. Preparation of 4-[[4-(4-cyanophenyl)butyl]amino]-4-oxo-3(R)-(1-pyrrolyl)butanoic acid To a solution of the product of step A (603 mg, 1.40 mmol) in methanol (5 mL) was added 5% Pd/C (100 mg). The reaction mixture was stirred at room temperature under a balloon of hydrogen for 1 hour. The catalyst was removed and the solvent was evaporated under reduced pressure. The residue was dissolved in 5% KHCO₃ and washed with ether. The aqueous phase was acidified to a pH of 1 (solid NaHSO₄) and extracted with ethyl acetate affording 362 mg (76%) of gummy product.

¹H-NMR (300 MHz, CDCl₃) δ1.35–1.60 (m, 4H), 2.64 (t, J=7 Hz, 2H), 2.95 (dd, J=7 Hz, J=16 Hz, 1H), 3.10–3.27 (m, 2H), 3.43 (dd, J=6 Hz, J=16 Hz, H), 5.05 (t, J=7 Hz, 1H), 5.37 (br.t, 1H, exchangeable) 6.25 (t, J=2 Hz, 2H), 6.69 (t, J=2 Hz, 2H), 7.23 (d, J=8 Hz, 2H), 7.57 (d, J=8 Hz, 2H).

D. Preparation of 4-[[4-4-(aminoiminomethyl)phenyl]butyl]amino]-4-oxo-3(R)-(1-pyrrolyl)butanoic acid The title compound was prepared from the product of step B (332 mg, 0.978 mmol) in a manner similar to example 3, step C affording 200 mg (57%) of gummy product.

¹H-NMR (300 MHz, CD₃OD/1 drop 6N DCl/D₂O) δ1.40–1.65 (m, 4H), 2.69 (t, J=7 Hz, 2H), 2.86 (dd, J=7 Hz, J=17 Hz, 1H), 3.10–3.30 (m, 3H), 5.03 (m, 1H), 6.08 (t, J=2 Hz, 2H), 6.69 (t, J=2 Hz, 2H), 7.41 (d, J=8 Hz, 2H), 7.72 (d, J=8 Hz, 2H).

EXAMPLE 16

Preparation of 4R-amino-5-[[4-[4-(aminoiminomethyl)phenyl]butyl]amino]-5-oxopentanoic acid, dihydrochloride

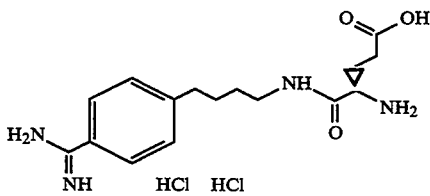

To a solution of the product of example 5, step B (100 mg, 0.22 mmol) and 2N HCl (220 μL) in methanol (5 mL) was added 5% Pd/C (100 mg). The reaction was stirred under a balloon of hydrogen for 1 hour. The catalyst was removed and the solvent evaporated under reduced pressure. Trituration of the residue with acetonitrile afforded 60 mg of product (70%).

Anal. calc'd. for $C_{16}H_{28}N_4O_3Cl_2 \cdot 1H_2O$: C, 46.72; H, 6.86; N, 13.62. Found: C, 46.81; H, 6.49; N, 13.79. ¹H-NMR (300 MHz, DMSO) δ1.40–1.55 (m, 2H), 1.55–1.70 (m, 2H), 1.95 (m, 2H), 2.32 (t, J=7 Hz, 2H), 2.70 (t, J=7 Hz, 2H) 3.05–3.25 (m, 2H), 3.80 (br.t, J=6 Hz, 1H), 7.45 (d, J=8 Hz, 2H), 7.79 (d, J=8 Hz, 2H)

EXAMPLE 17

Preparation of 4-[[4-[4-(aminoiminomethyl)phenyl]butyl]amino]-4-oxo-3(R)-methylbutanoic acid A. Preparation of 1,1-dimethyl 4-[[4-(4-cyanophenyl)butyl]amino]-4-oxo-3(R)-methylbutanoate The title compound is synthesized by the method described in Example 1, Step D, substituting 2(R)-methylbutanedioic acid 4-t-butyl ester [For synthesis of this and related compounds see: Oppolzer, W., Rodriguez, I., Starkemann, C., Walher, E., *Tetrahedron Letters* 31, 5019–22, (1990)] for the aspartic acid derivative.

B. Preparation of 4-[[4-[4-(aminoiminomethyl)phenyl]butyl]amino]-4-oxo-3(R)-methylbutanoic acid The title compound is prepared from the product of Step A in a manner similar to Example 1, step E.

EXAMPLE 18

The platelet-binding inhibitor activity of the compounds of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975× g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000× g for 15 minutes at room temperature allowing the centrifuge to coast to a stop without braking. The PRP was adjusted with PPP to a count of 2–3×$10^8$ platelets per ml. 400 μl of the PRP preparation and 50 μl of the compound to be tested or saline were preincubated for 1 minute at 37° C. in a BioData aggregometer (BioData, Horsham, Pa.). 50 μl of adenosine 5'diphosphate (ADP) (50 μm final concentration) was added to the cuvettes and the aggregation was monitored for 1 minute. All compounds are tested in duplicate. Results are calculated as follows:

Percent of control = [(maximal OD minus initial OD of compound) divided by (maximal OD minus initial OD of control saline)] × 100. The % inhibition = 100 − (percent of control).

The compounds tested and their median inhibitory concentrations ($IC_{50}$) are recorded in Table I. $IC_{50}$'s (if a compound showed 50% inhibition) were calculated by linear regression of the dose response curve.

The assay results for the compounds of the present invention are set forth in Table A, below.

INHIBITION OF EX VIVO COLLAGEN INDUCED AGGREGATION BY COMPOUNDS OF THE INVENTION

PURPOSE—The purpose of this assay is to determine the effects of antiplatelet compounds on ex vivo collagen induced platelet aggregation when administered either intravenously or orally to dogs.

Pretreatment (control) blood samples are drawn from either conscious or anesthetized dogs (Beagles) and centrifuged to prepare platelet rich plasma (PRP). Aggregatory response to collagen is measured in an aggregometer and used as control. Compounds are administered, either intragasterically (either by capsule or stomach tube or intravenously. Blood samples are drawn at predetermined intervals after compound administration, PRP prepared and aggregation to collagen determined. Compound inhibition of aggregation is determined by comparing the aggregation response after compound administration to the pretreatment response. The study is continued for a maximum of 24 hours or until the platelet aggregation returns to control levels. (If aggregation is still inhibited after 7 hours, a blood sample is drawn the following morning and tested.) Duration of activity is determined by the length of time platelet aggregation is inhibited after compound administration. The assay results for representative compounds of the present invention in the aforementioned Assay are set forth in Table A.

In Table A, two readings given in a single box indicate that two trials, rather than a single trial, were run for that particular compound in that particular assay.

TABLE A

| | IN-VITRO PLATELET AGGREGATION IN PRP | | | EX-VIVO COLLAGEN INDUCED AGGREGATION | | |
|---|---|---|---|---|---|---|
| Compound | Dog PRP $IC_{50}$ Micro M | % Inhibition | Test Concentration | Dose Tested mg/Kg | Max % Inhibition | Duration Hours |
| 52513 4-[[4-[4-(aminoiminomethyl)phenyl] butyl]amino]-4-oxo-3R-[[(phenylmethoxy) carbonyl]amino]butanoic acid | 3.0 | 100 | 1 × $10^{-5}$ | 3 × $10^{-4}$ IV | 100 | |
| 52809 5-[[4-[4-(aminoiminomethyl)phenyl]butyl] amino]-5-oxo-4R-[[(phenylmethoxy) carbonyl]amino]pentanoic acid | 1.8 | 100 | 1 × $10^{-5}$ | 3 × $10^{-4}$ IV | 46 | |
| 52828 5-[[4-[4-(aminoiminomethyl)phenyl]butyl] amino]-5-oxo-4S-[[(phenylmethoxy) carbonyl]amino]pentanoic acid | 4.2 | 77 | 1 × $10^{-5}$ | 3 × $10^{-4}$ IV | 100 | |
| 53112 5-[[4-[4-(aminoiminomethyl)phenyl] butyl]amino]-5-oxo-4S-[1-oxo-3- phenylpropylamino]pentanoic acid | 1.9 | | | | | |
| 53143 4-[[4-[4-(aminoiminomethyl)phenyl] butyl]amino]-4-oxo-3R-[(1-oxo-3- phenylpropyl)amino]butanoic acid | 4.1 | 100 | 1 × $10^{-5}$ | | | |
| 53314 5-[[5-[4-aminoiminomethyl]phenyl]-4- pentynyl]amino]-5-oxo-4R-[[(phenyl methoxy)carbonyl]amino]pentanoic acid | 2.0 | 100 | 1 × $10^{-5}$ | | | |

TABLE A-continued

| | IN-VITRO PLATELET AGGREGATION IN PRP | | | EX-VIVO COLLAGEN INDUCED AGGREGATION | | | |
|---|---|---|---|---|---|---|---|
| 53033<br>ethyl 5-[[4-[4-(aminoiminomethyl)phenyl]butyl]amino]-5-oxo-4R-[[(phenylmethoxy)carbonyl]amino]pentanoate, monohydrochloride | 7.0 | 100 | $1 \times 10^{-5}$ | | | | |
| 53065<br>5-[[4-[4-(aminoiminomethyl)phenyl]butyl]amino]-5-oxo-4R-[(methylsulfonyl)amino]pentanoic acid | 3.5 | 100 | $1 \times 10^{-5}$ | | | | |
| 53175<br>ethyl 5-[[4-[4-(aminoiminomethyl)phenyl]butyl]amino]-5-oxo-4R-[(methylsulfonyl)amino]pentanoate, monohydrochloride | NT | NT | NT | | | | |
| 53010<br>4-[[4-[4-(aminoiminomethyl)phenyl]butyl]amino]-4-oxo-3R-[[(4-methylphenyl)sulfonyl]amino]butanoic acid | 6.0 | 100 | $1 \times 10^{-5}$ | | | | |
| 52554<br>4-[[4-[4-(aminoiminomethyl)phenyl]butyl]amino]-4-oxo-3R-(1H-pyrrol-1-yl)butanoic acid, monohydroiodide | | 15 | $1 \times 10^{-5}$ | | | | |
| | | 82 | $1 \times 10^{-4}$ | | | | |
| 53085<br>4R-amino-5-[[4-[4-(aminoiminomethyl)phenyl]butyl]amino]-5-oxopentanoic acid, dihydrochloride | | 18 | $1 \times 10^{-5}$ | | | | |
| | | 97 | $1 \times 10^{-4}$ | | | | |

The compounds of the present invention can be useful in a variety of therapeutic interventions, for example, preventing re-occlusion following re-canalization procedures such as post fibrinolytic therapy, thrombolytic therapy, angioplasty and coronary bypass surgery. Other potential uses are for prevention of myocardial infarct, recurrent myocardial infarct, unstable angina, peripheral artery disease, cerebral ischemia, stroke and diseases of platelet hyperaggregability, and to prevent occlusion in hemodialysis, shunt procedures, preventing the progression of atherosclerosis and preventing the recurrence of tumors at a local site after resection of tissue at that site.

What we claim is:

1. A compound of the formula

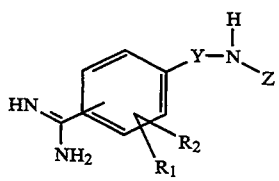

I or a pharmaceutically acceptable salt thereof, wherein
  $R_1$ and $R_2$ are each independently hydrido, alkyl having 1 to 6 carbon atoms, alkoxy having 1 to 6 carbon atoms or halo;
  Y is alkylene having 1 to 6 carbon atoms, alkenylene having 2 to 4 carbon atoms, alkynylene having 2 to 4 carbon atoms or carboxamidoalkyl wherein the alkyl is 1 to 6 carbon atoms and
  Z is a group having the formula

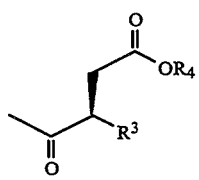

(Z1)

or

-continued

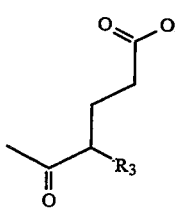

(Z2)

wherein
  $R_3$ is absent; alkyl having 1 to 6 carbon atoms; alkenyl having 2 to 4 carbon atoms; alkynyl having 2 to 4 carbon atoms; phenyl; substituted phenyl wherein each substituent is selected from the group consisting of alkyl having 1 to 6 carbon atoms, alkoxy having 1 to 6 carbon atoms and halo; phenylalkylamido wherein the alkyl is 1 to 6 carbon atoms and the alkyl chain may be interrupted by oxygen; substituted phenylalkylamido wherein the alkyl is 1 to 6 carbon atoms and the alkyl chain may be interrupted by oxygen and the phenyl substituents are selected from the group consisting of alkyl having 1 to 6 carbon atoms and alkoxy having 1 to 6 carbon atoms; hydroxy; amino; alkylsulfonamido wherein the alkyl is 1 to 6 carbon atoms; phenylsulfonamido; or substituted phenylsulfonamido wherein each phenyl substituent is selected from the group consisting of alkyl having 1 to 6 carbon atoms, alkoxy having 1 to 6 carbon atoms, and halo; and
  $R_4$ is absent, hydrido or alkyl having 1 to 6 carbon atoms with the understanding that when $R_4$ is absent, and $R_3$ is absent or alkyl having 1 or 2 carbon atoms, the oxygen adjacent to $R_4$ position can combine with $R_3$ when present or can combine with the carbon adjacent to the carbonyl to form a lactone; with the proviso that when Y is alkyl having three carbon atoms Z is $Z_1$.

2. A compound according to claim 1 of the formula

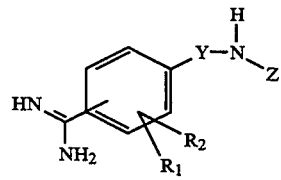

I or a pharmaceutically acceptable salt thereof, wherein
R₁ and R₂ are each independently hydrido, alkyl having 1 to 6 carbon atoms, alkoxy having 1 to 6 carbon atoms or halo;
Y is alkylene having 1 to 6 carbon atoms, alkenylene having 2 to 4 carbon atoms or alkynylene having 2 to 4 carbon atoms;
Z is a group having the formula

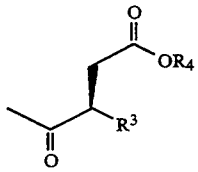  (Z₁)

or

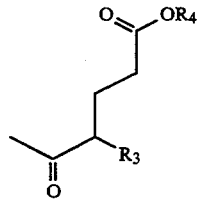  (Z₂)

wherein
R₃ is phenylalkylamido wherein the alkyl is 1 to 6 carbon atoms and the alkyl chain may be interrupted by oxygen; substituted phenylalkylamido wherein the alkyl is 1 to 6 carbon atoms and the alkyl chain may be interrupted by oxygen and the phenyl substituents are selected from the group consisting of alkyl having 1 to 6 carbon atoms and alkoxy having 1 to 6 carbon atoms; and
R₄ is hydrido or alkyl having 1 to 6 carbon atoms.

3. A compound according to claim 1 of the formula

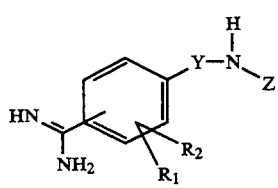  I or a pharmaceutically acceptable salt thereof, wherein
R₁ and R₂ are each independently hydrido, alkyl having 1 to 6 carbon atoms, alkoxy having 1 to 6 carbon atoms or halo;
Y is alkylene having 1 to 6 carbon atoms, alkenylene having 2 to 4 carbon atoms or alkynylene having 2 to 4 carbon atoms;
Z is a group having the formula

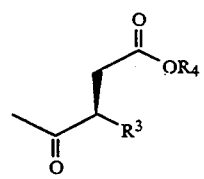  (Z₁)

or

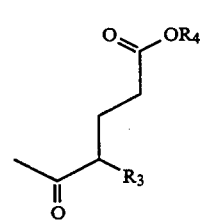  (Z₂)

wherein
R₃ is alkylsulfonamido wherein the alkyl is 1 to 6 carbon atoms; phenylsulfonamido, or substituted phenylsulfonamido wherein each phenyl substituent is selected from the group consisting of alkyl having 1 to 6 carbon atoms and alkoxy having 1 to 6 carbon atoms; and
R₄ is hydrido or alkyl having 1 to 6 carbon atoms.

4. A compound according to claim 1 wherein R₄ is absent with the understanding that when R₄ is absent, R₃ is absent or alkyl having 1 or 2 carbon atoms, the oxygen adjacent to the R₄ position can combine with R₃ when present or can combine with the carbon adjacent to the carbonyl to form a lactone.

5. A compound according to claim 1 which is 5-[[4-[4- (aminoiminomethyl)phenyl]butyl]amino]-4R-hydroxy-5-oxopentanoic acid.

6. A compound according to claim 1 which is 4R-amino-5-[[4-[4-(aminoiminomethyl)phenyl]butyl]amino]-5-oxopentanoic acid, dihydrochloride.

7. A compound according to claim 2 which is 4-[[4-[4-(aminoiminomethyl)phenyl]butyl]amino]-4-oxo-3R-[[(phenylmethoxy)carbonyl]amino]butanoic acid.

8. A compound according to claim 2 which is 5-[[4-[4-(aminoiminomethyl)phenyl]butyl]amino]-5-oxo-4R-[[(phenylmethoxy)carbonyl]amino]pentanoic acid.

9. A compound according to claim 2 which is 5-[[4-[4-(aminoiminomethyl)phenyl]butyl]amino]-5-oxo-4S-[[(phenylmethoxy)carbonyl]amino]pentanoic acid.

10. A compound according to claim 2 which is 5-[[4-[4-(aminoiminomethyl)phenyl[butyl]amino]-5-oxo-4S-[1-oxo-3-phenylpropylamino]pentanoic acid.

11. A compound according to claim 2 which is 4-[[4-[4-(aminoiminomethyl)phenyl]butyl]amino]-4-oxo-3R-[(1-oxo-3-phenylpropyl)amino]butanoic acid.

12. A compound according to claim 2 which is 5-[[5-[4-aminoiminomethyl)phenyl]-4-pentynyl]amino]-5-oxo-4R-[[(phenyl methoxy)carbonyl]amino]pentanoic acid.

13. A compound according to claim 2 which is ethyl 5-[[4-[4-(aminoiminomethyl)phenyl]butyl]amino]-5-oxo-4R-[[(phenylmethoxy)carbonyl]amino]pentanoate, monohydrochloride.

14. A compound according to claim 3 which is 5-[[4-[4-(aminoiminomethyl)phenyl]butyl]amino-5-oxo-4R-[(methylsulfonyl)amino]pentanoic acid.

15. A compound according to claim 3 which is ethyl 5-[[4-[4-(aminoiminomethyl)phenyl]butyl]amino]-5-oxo-4R-[(methylsulfonyl)amino]pentanoate, monohydrochloride.

16. A compound according to claim 3 which is 4-[[4-[4-(aminoiminomethyl)phenyl]butyl]amino]-4-oxo-3R-[[(4-methylphenyl)sulfonyl]amino]butanoic acid.

17. A pharmaceutical composition useful for inhibiting platelet aggregation comprising an effective amount of at least one compound according to claim 1, together with one or more non-toxic pharmaceutically acceptable carriers.

18. A pharmaceutical composition according to claim 17 wherein the compound has the formula

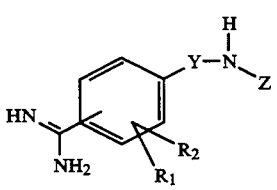  I or a pharmaceutically acceptable salt thereof, wherein
R₁ and R₂ are each independently hydrido, alkyl having 1 to 6 carbon atoms, alkoxy having 1 to 6 carbon atoms or halo;

Y is alkylene having 1 to 6 carbon atoms, alkenylene having 2 to 4 carbon atoms or alkynylene having 2 to 4 carbon atoms;

Z is a group having the formula

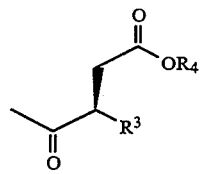
(Z₁)

or

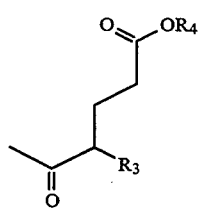
(Z₂)

wherein
R₃ is phenylalkylamido wherein the alkyl is 1 to 6 carbon atoms and the alkyl chain may be interrupted by oxygen; substituted phenylalkylamido wherein the alkyl is 1 to 6 carbon atoms and the alkyl chain may be interrupted by oxygen and the phenyl substituents are selected from the group consisting of alkyl having 1 to 6 carbon atoms and alkoxy having 1 to 6 carbon atoms; and R₄ is hydrido or alkyl having 1 to 6 carbon atoms.

19. A pharmaceutical composition according to claim 17 wherein the compound has the formula

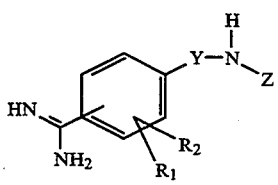
I or a pharmaceutically acceptable salt thereof, wherein
R₁ and R₂ are each independently hydrido, alkyl having 1 to 6 carbon atoms, alkoxy having 1 to 6 carbon atoms or halo;

Y is alkylene having 1 to 6 carbon atoms, alkenylene having 2 to 4 carbon atoms or alkynylene having 2 to 4 carbon atoms;

Z is a group having the formula

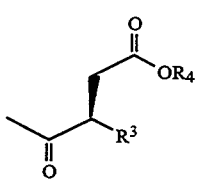
(Z₁)

or

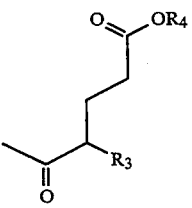
(Z₂)

wherein
R₃ is alkylsulfonamido wherein the alkyl is 1 to 6 carbon atoms; phenylsulfonamido, or substituted phenylsulfonamido wherein each phenyl substituent is selected from the group consisting of alkyl having 1 to 6 carbon atoms and alkoxy having 1 to 6 carbon atoms; and R₄ is hydrido or alkyl having 1 to 6 carbon atoms.

20. A pharmaceutical composition according to claim 18 wherein said compound is selected from the group consisting of
4-[[4-[4-(aminoiminomethyl)phenyl]butyl]amino]-4-oxo-3R-[[(phenylmethoxy)carbonyl]amino]butanoic acid;

5-[[4-[4-(aminoiminomethyl)phenyl]butyl]amino]-5-oxo-4R-[[(phenylmethoxy)carbonyl]amino]pentanoic acid;

4-[[4-[4-(aminoiminomethyl)phenyl]butyl]amino]-4-oxo-3R-[(1-oxo-3-phenylpropyl)amino]butanoic acid;

5-[[5-[-4-aminoiminomethyl)phenyl]-4-pentynyl-]amino]-5-oxo-4R-[[(phenylmethoxy)carbonyl-]amino]pentanoic acid; or ethyl 5-[[4-[4-(aminoiminomethyl)phenyl]butyl]amino]-5-oxo-4R-[[(phenylmethoxy)carbonyl]amino]pentanoate, monohydrochloride.

21. A pharmaceutical composition according to claim 19 wherein the compound is 4-[[4-[4-(aminoiminomethyl)phenyl]butyl]amino]-4-oxo-3R-[[(4-methylphenyl)-sulfonyl]amino]butanoic acid.

22. A method of treating a mammal to inhibit platelet aggregation comprising administering a therapeutically effective dose of at least one compound of claim 1 to a mammal in need of such treatment.

23. A method according to claim 22 wherein the compound has the formula

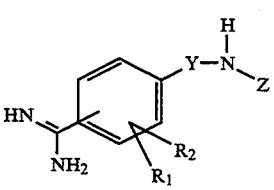
I or a pharmaceutically acceptable salt thereof, wherein
R₁ and R₂ are each independently hydrido, alkyl having 1 to 6 carbon atoms, alkoxy having 1 to 6 carbon atoms or halo;

Y is alkylene having 1 to 6 carbon atoms, alkenylene having 2 to 4 carbon atoms or alkynylene having 2 to 4 carbon atoms;

Z is a group having the formula

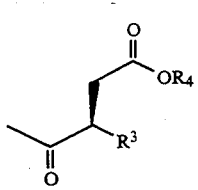
(Z₁)

or

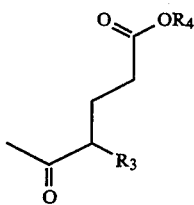
(Z₂)

wherein

R₃ is phenylalkylamido wherein the alkyl is 1 to 6 carbon atoms and the alkyl chain may be interrupted by oxygen; substituted phenylalkylamido wherein the alkyl is 1 to 6 carbon atoms and the alkyl chain may be interrupted by oxygen and the phenyl substituents are selected from the group consisting of alkyl having 1 to 6 carbon atoms and alkoxy having 1 to 6 carbon atoms; and R₄ is hydrido or alkyl having 1 to 6 carbon atoms.

24. A method according to claim 22 wherein the compound has the formula

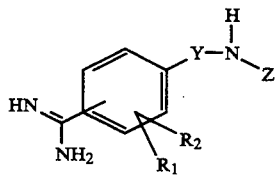
I or a pharmaceutically acceptable salt thereof, wherein

R₁ and R₂ are each independently hydrido, alkyl having 1 to 6 carbon atoms, alkoxy having 1 to 6 carbon atoms or halo;

Y is alkylene having 1 to 6 carbon atoms, alkenylene having 2 to 4 carbon atoms or alkynylene having 2 to 4 carbon atoms;

Z is a group having the formula

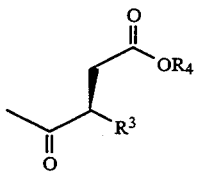
(Z₁)

or

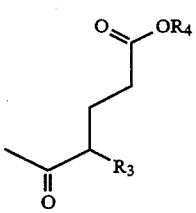
(Z₂)

wherein

R₃ is alkylsulfonamido wherein the alkyl is 1 to 6 carbon atoms; phenylsulfonamido, or substituted phenylsulfonamido wherein each phenyl substituent is selected from the group consisting of alkyl having 1 to 6 carbon atoms and alkoxy having 1 to 6 carbon atoms; and R₄ is hydrido or alkyl having 1 to 6 carbon atoms.

25. A method according to claim 23 wherein the compound is selected from the group consisting of
4-[[4-[4-(aminoiminomethyl)phenyl]butyl]amino]-4-oxo-3R-[[(phenylmethoxy)carbonyl]amino]butanoic acid;

5- [[4-[4-(aminoiminomethyl)phenyl]butyl]amino]-5-oxo-4R-[[(phenylmethoxy)carbonyl]amino]pentanoic acid;

4-[[4-[4-(aminoiminomethyl)phenyl]butyl]amino]-4-oxo-3R-[(1-oxo-3-phenylpropyl)amino]butanoic acid;

5-[[5-[4-(aminoiminomethyl)phenyl]-4-pentynyl-]amino]-5-oxo-4R-[[(phenylmethoxy)carbonyl-]amino]pentanoic acid; or ethyl 5-[[4-[4-(aminoiminomethyl)phenyl]butyl]amino]-5-oxo-4R-[[(phenylmethoxy)carbonyl]amino]pentanoate, monohydrochloride.

26. A method according to claim 24 wherein the compound is 4-[[4-[4-(aminoiminomethyl)phenyl]butyl-]amino]-4-oxo-3R-[[(4-methylphenyl)sulfonyl]amino]-butanoic acid.

* * * * *

UNITED STATES PATENT AND TRADEMARK OFFICE
CERTIFICATE OF CORRECTION

PATENT NO. : 5,424,334  Page 1 of 2
DATED : June 13, 1995
INVENTOR(S) : Abood, et al.

It is certified that error appears in the above-indentified patent and that said Letters Patent is hereby corrected as shown below:

Column 1, line 52, reading "Hayerstick" should read --Haverstick--.

Column 1, line 55, reading "497-497" should read --491-497--.

Column 22, line 50, reading "cyanphenyl" should read --cyanophenyl--.

Column 24, line 57, that part of the formula reading

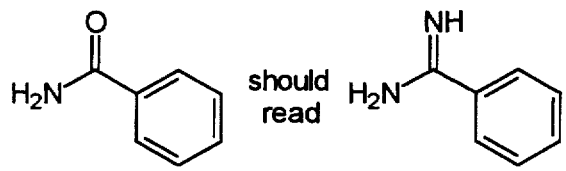

Column 26, line 13, that part of the formula reading

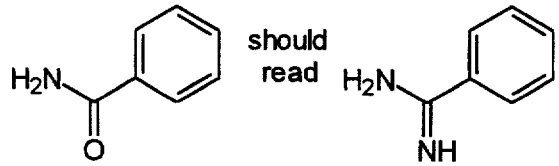

UNITED STATES PATENT AND TRADEMARK OFFICE
CERTIFICATE OF CORRECTION

PATENT NO. : 5,424,334        Page 2 of 2
DATED     : June 13, 1995
INVENTOR(S) : Abood, et al.

It is certified that error appears in the above-indentified patent and that said Letters Patent is hereby corrected as shown below:

Column 27, line 15, that part of the formula reading

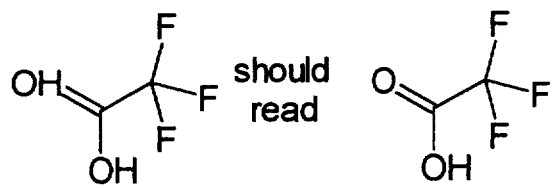

Signed and Sealed this

Ninth Day of December, 1997

Attest:

BRUCE LEHMAN

Attesting Officer        Commissioner of Patents and Trademarks